US010612073B2

(12) United States Patent
Fujioka

(10) Patent No.: US 10,612,073 B2
(45) Date of Patent: Apr. 7, 2020

(54) METHOD FOR CONSTRUCTING NUCLEIC ACID MOLECULE

(71) Applicant: Hitachi High-Technologies Corporation, Minato-ku, Tokyo (JP)

(72) Inventor: Michiru Fujioka, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 243 days.

(21) Appl. No.: 15/550,144

(22) PCT Filed: Feb. 26, 2016

(86) PCT No.: PCT/JP2016/055850
§ 371 (c)(1),
(2) Date: Aug. 10, 2017

(87) PCT Pub. No.: WO2016/136952
PCT Pub. Date: Sep. 1, 2016

(65) Prior Publication Data
US 2018/0030506 A1    Feb. 1, 2018

(30) Foreign Application Priority Data

Feb. 26, 2015  (WO) ................ PCT/JP2015/055529

(51) Int. Cl.
| | | |
|---|---|---|
| *C12P 19/34* | (2006.01) | |
| *C12Q 1/6806* | (2018.01) | |
| *C12Q 1/6869* | (2018.01) | |
| *C12Q 1/6853* | (2018.01) | |
| *G01N 33/487* | (2006.01) | |

(52) U.S. Cl.
CPC ......... *C12Q 1/6806* (2013.01); *C12Q 1/6853* (2013.01); *C12Q 1/6869* (2013.01); *G01N 33/48721* (2013.01)

(58) Field of Classification Search
CPC ........ C12Q 2525/161; C12Q 2525/301; C12Q 2527/107; C12Q 2531/113; C12Q 1/6806; C12Q 1/6853; C12Q 1/6869; G01N 33/48721
See application file for complete search history.

(56) References Cited

U.S. PATENT DOCUMENTS

| | | | |
|---|---|---|---|
| 2007/0020640 A1 | 1/2007 | McCloskey et al. | |
| 2013/0244340 A1* | 9/2013 | Davis | G01N 33/48721 436/501 |

FOREIGN PATENT DOCUMENTS

| | | |
|---|---|---|
| EP | 2 058 392 A1 | 5/2009 |
| JP | 10-510161 A | 10/1998 |
| JP | 2010-538633 A | 12/2010 |
| JP | 2011-515102 A | 5/2011 |
| JP | 2012-516146 A | 7/2012 |
| JP | 2012-529904 A | 11/2012 |
| JP | 2014-531196 A | 11/2014 |
| WO | WO 96/17079 A1 | 6/1996 |
| WO | WO 2008/026582 A1 | 3/2008 |
| WO | WO 2009/037438 A1 | 3/2009 |
| WO | WO 2009/120372 A2 | 10/2009 |
| WO | WO 2010/086622 A1 | 8/2010 |
| WO | WO 2010/146349 A1 | 12/2010 |
| WO | WO 2013/014451 A1 | 1/2013 |
| WO | WO 2013/185137 A | 12/2013 |
| WO | WO 2014/052487 A1 | 4/2014 |

OTHER PUBLICATIONS

International Search Report (PCT/ISA/210) issued in PCT Application No. PCT/JP2016/055850 dated May 24, 2016 with English translation (Four (4) pages).
Japanese-language Written Opinion (PCT/ISA/237) issued in PCT Application No. PCT/JP2016/055850 dated May 24, 2016 (Four (4) pages).
Japanese-language Office Action issued in counterpart Japanese Application No. 2017-502514 dated Oct. 16, 2018 with English translation (four (4) pages).
Japanese-language Office Action issued in counterpart Japanese Application No. 2017-502514 dated Apr. 9, 2019 with unverified translation (seven pages).

* cited by examiner

*Primary Examiner* — Cynthia B Wilder
(74) *Attorney, Agent, or Firm* — Crowell & Moring LLP

(57) ABSTRACT

The present invention provides a method for constructing a single-stranded nucleic acid molecule for nucleic acid sequencing by means of a nanopore sequencer, said method including: a step in which at least one hairpin primer including a single-stranded region on the 3' side and a pair of primers are used to synthesize a complementary strand of template DNA that includes the target sequence; and a step in which the synthesized complementary strand forms a hairpin structure inside a molecule and a template extension reaction is carried out. The obtained nucleic acid molecule includes both the target sequence and the complementary strand thereof in the sequence. Single strand construction enables analysis by nanopore sequencing, and the sequence of only the target nucleic acid, which does not include information of the complementary strand, is repeatedly analyzed, thus enabling analysis to be conducted with greater precision by addressing the problem of sequence errors.

16 Claims, 11 Drawing Sheets

Specification includes a Sequence Listing.

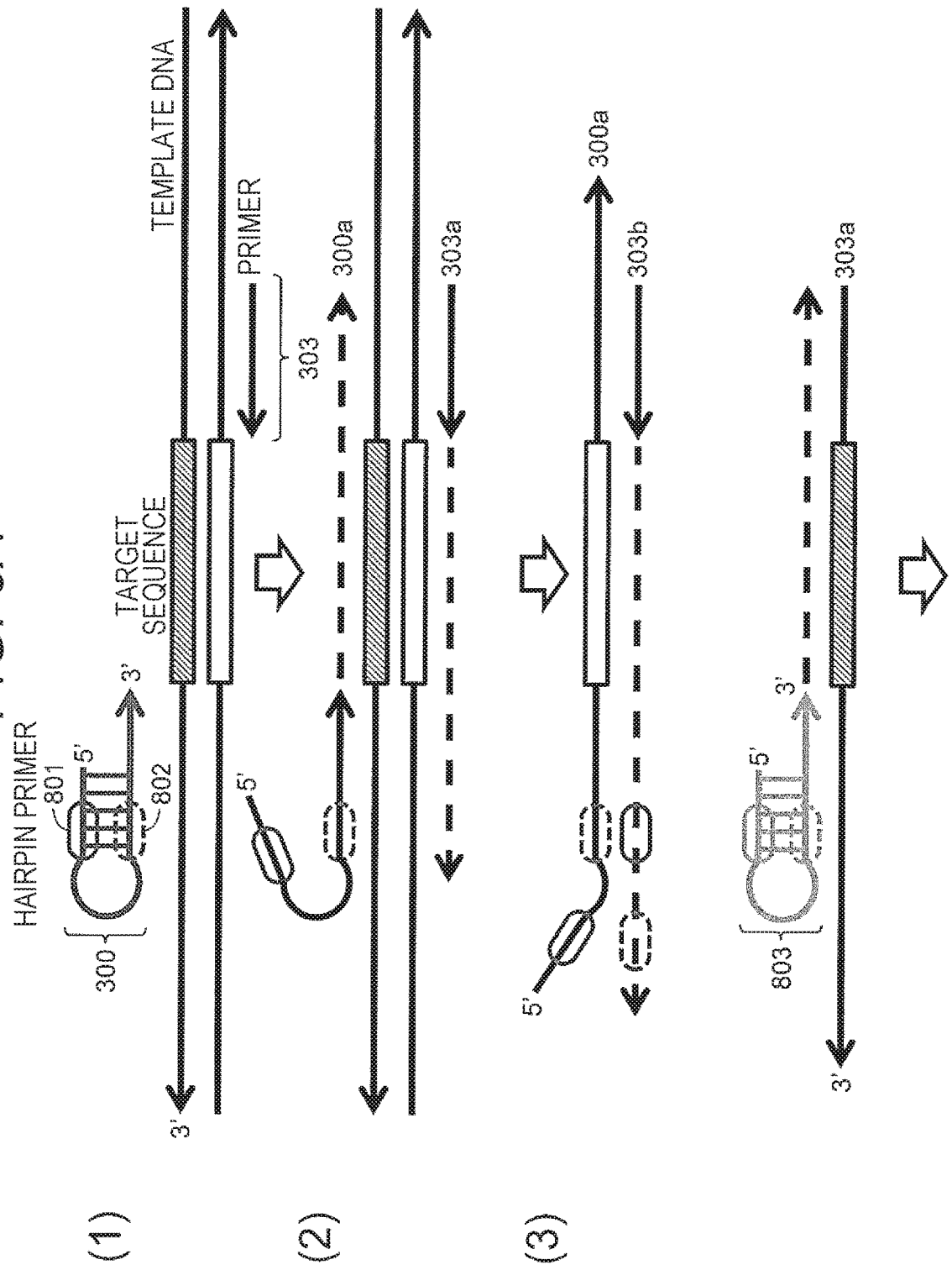

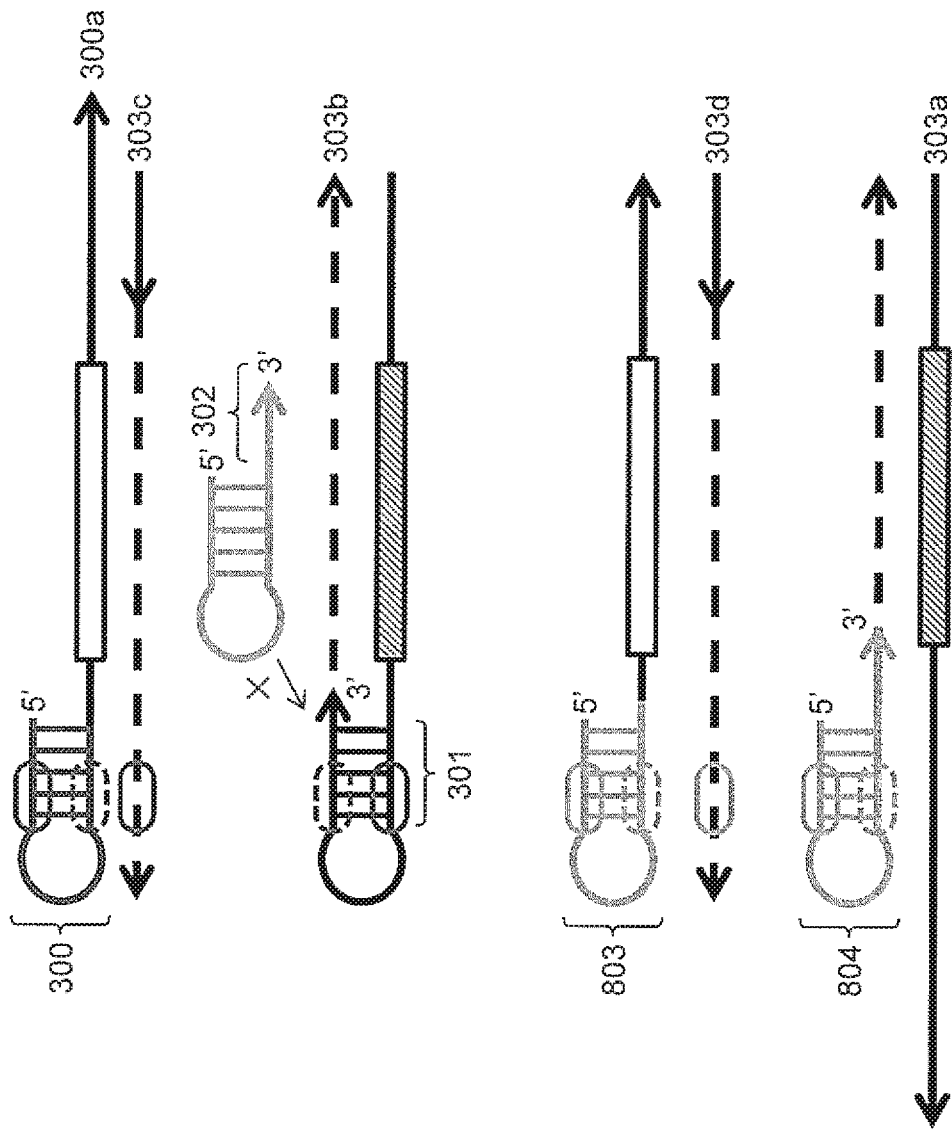

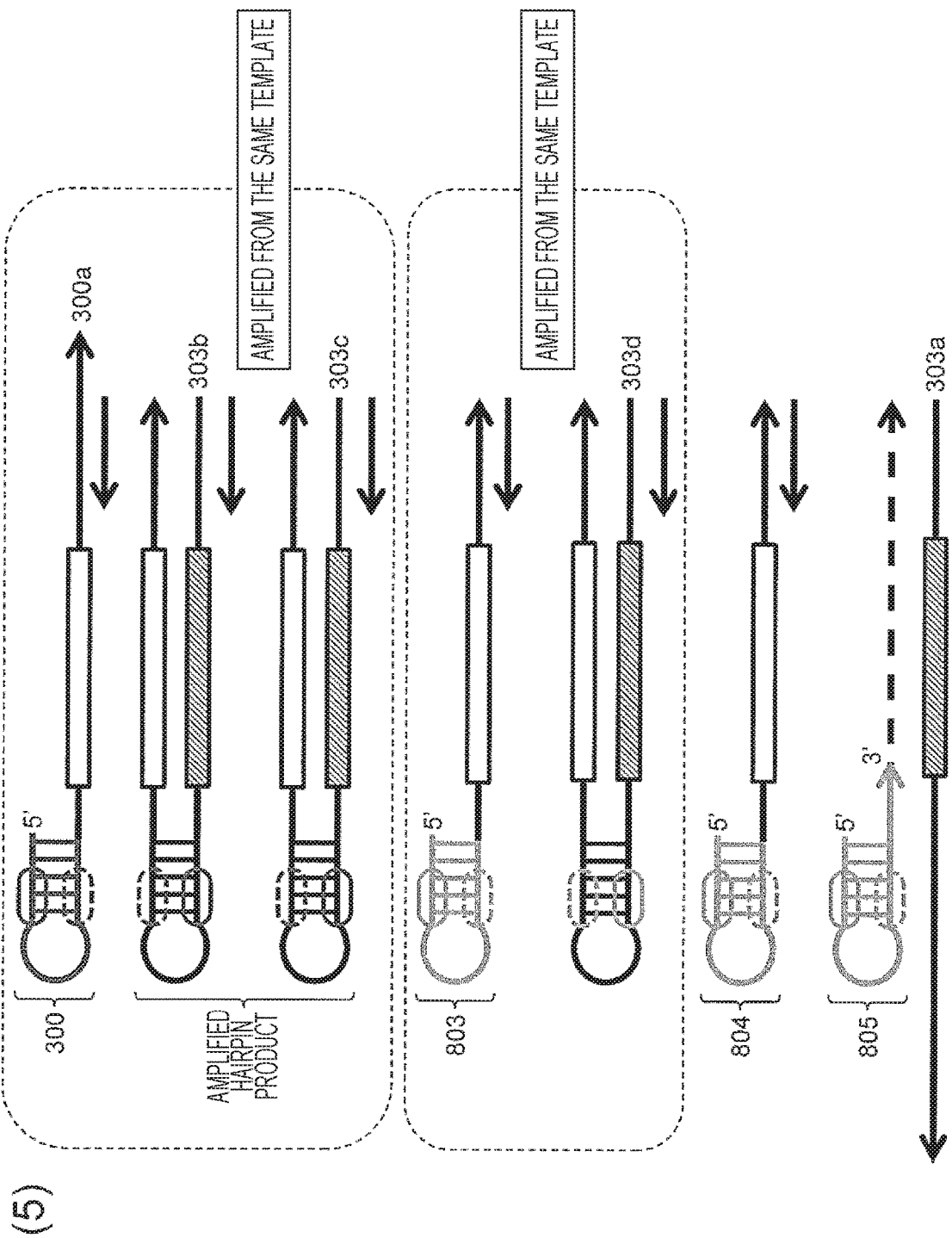

FIG. 9

| | | | | | | | | | | |
|---|---|---|---|---|---|---|---|---|---|---|
| REFERENCE SEQUENCE | ... | AGTC | AGTC | AGTC | AGTC | AGTC | AGTC | AGTC | | | |
| AMPLIFIED NUCLEIC ACID MOLECULE 01 | ... | AGTC | AGTC | AGTC | AGTC | AGCC | AGTC | AGTC | AGAT TCGG | (SEQ ID No. 4) |
| AMPLIFIED NUCLEIC ACID MOLECULE 02 | ... | AGTG | AGTC | AGTC | AGTC | AGCC | AGTC | AGTC | AGAT TCGG | (SEQ ID No. 5) |
| AMPLIFIED NUCLEIC ACID MOLECULE 03 | ... | AGTC | AGTC | AGTC | AGTC | AGCC | AGTC | AGTC | AGAT TCGG | (SEQ ID No. 6) |
| AMPLIFIED NUCLEIC ACID MOLECULE 04 | ... | AGTC | AGTC | TGTC | AGTC | AGCC | AGTC | AGTC | AGAT TCGG | (SEQ ID No. 7) |
| AMPLIFIED NUCLEIC ACID MOLECULE 05 | ... | AGTC | AGTC | AGTC | AGTC | AGCC | AGTC | AGCC | AGAT TCGG | (SEQ ID No. 8) |

901, 902

METHOD FOR CONSTRUCTING NUCLEIC ACID MOLECULE

TECHNICAL FIELD

The present invention relates to a method for constructing a nucleic acid molecule for nucleic acid sequencing. More specifically, the present invention relates to a method for constructing a single-stranded nucleic acid molecule that is suitable for analysis by nanopore sequencing.

BACKGROUND ART

In recent years, a demand for the analysis of nucleic acid base sequences has been considerably increasing for the purpose of detecting causative genes of genetic diseases, evaluating effectiveness or side effect of drugs, detecting genetic mutation involved in cancerous diseases, or the like. Therefore, information obtained from the results of analysis needs to have high precision.

As a method of reading a base sequence of a nucleic acid molecule with high precision, for example, there is proposed a method of determining a consensus sequence of nucleotides in a template nucleic acid segment, the method including: providing a sense strand and an antisense strand of the template nucleic acid segment in a contiguous nucleic acid molecule; and sequencing both the sense strand and the antisense strand in a polymerase mediated, template dependent sequencing process (PTL 1). In PTL 1, it is described that "By virtue of the circular nature of the template structure, repeated sequencing of the same molecule can be performed in plural times. In other words, the sequencing process progresses around a completely contiguous sequence, and each segment from the complementary sequences is repeatedly sequenced so that sequence data of the segment and sequence data in each segment can be repeatedly obtained. All or portions of such sequence data are then useful in deriving a consensus sequence for the template and its various segments" (Paragraph [0055]).

In addition, PTL 2 discloses adapters that include a double-stranded nucleic acid region and are usable for generating single-stranded constructs of nucleic acid for sequencing purpose. In PTL 2, it is described that "This ensures that, when the construct is sequenced, each position in the double-stranded nucleic acid is not merely observed once, but is in fact interrogated twice. This gives greater certainty that each position in the nucleic acid has been observed and that the aggregate call for both bases at each position is of a greater quality score than would be possible with a single observation" (Paragraph [0038]). It is further described that "The ability to interrogate each position twice is also helpful for differentiating between methylcytosine and thymine using stochastic sensing. These two bases result in very similar current traces when they pass through and interact with a transmembrane pore. It can therefore be difficult to differentiate between the two. However, interrogation of each position in a nucleic acid twice will allow such differentiation because the complementary base for methylcytosine is guanine, whereas the complementary base for thymine is adenine. Methylcytosine has of course been linked with various diseases, including cancer" (Paragraph [0042]).

CITATION LIST

Patent Literature

PTL 1: Japanese Translation of PCT International Application Publication No. 2011-515102
PTL 2: Japanese Translation of PCT International Application Publication No. 2012-516146

SUMMARY OF INVENTION

Technical Problem

The technique described in PTL 1 relates to a molecule in which one terminal of a double-stranded nucleic acid is coupled with a hairpin loop or a circular molecule in which both terminals are coupled with a hairpin loop. The molecule in which one terminal is coupled improves the determination precision of a base by using two results obtained by respectively reading each sequence of complementary strands (a sense strand and an antisense strand) once. However, in this technique, in a case where a mutation like a mismatched base pair exists in one nucleic acid strand or in a case where a sequence error occurs, only by reading each sequence of complementary strands once, a difference in the results between sequences of the complementary strands occurs.

In a case where such a difference occurs, it is not possible to determine whether there is a mutation or a sequence error occurs at the site where the difference occurs. Thus, a problem arises in that analysis with high certainty cannot be performed only by interrogating each base of the complementary strands once. Further, in a circular molecule in which both terminals are coupled with a hairpin loop, a problem of sequencing error may be solved by repeatedly performing sequencing over and over again as in the patent literature; however, there is a problem in that the circular molecule cannot be analyzed by a nanopore sequencing method of analyzing a single-stranded nucleic acid.

Also in PTL 2, similarly, since the technique relates to a molecule in which one terminal of a double-stranded nucleic acid is coupled with a hairpin loop, there is a problem in that it is not possible to determine whether there is a mutation or a sequence error occurs only by similarly interrogating each complementary strand once. Further, since a ligation reaction or the like is performed in order to form a hairpin loop, the efficiency of constructing a nucleic acid molecule to which a hairpin loop is correctly bound is low. It is also possible to perform a reaction overnight (for example, 8 hr or longer) in order to enhance the efficiency, but a problem also arises in that a time for pre-treatment is required.

Solution to Problem

In order to solve the above-described problems, the present inventors have been studied a method for constructing a nucleic acid molecule having a sequence structure in which only a base sequence of one side as a target in a single-stranded nucleic acid (single molecule) is repeated, and have completed the present invention. With the single strand structure, analysis by nanopore sequencing can be performed, and the sequence of only the target nucleic acid not including complementary strand information is repeatedly analyzed. Thus, it is possible to deal with a sequence error problem and to perform analysis with higher precision. As the number of repeated times of the sequence in the molecule increases, determination precision is improved.

That is, the present invention includes the description below.

[1] A method for constructing a single-stranded nucleic acid molecule for nucleic acid sequencing by means of a nanopore sequencer, the method including:

a step in which at least one hairpin primer including a single-stranded region at the 3' terminal and a primer in a pair with the hairpin primer are used to synthesize a complementary strand of a template DNA including a target sequence; and a step in which the synthesized complementary strand forms a hairpin structure inside a molecule and a template extension reaction is carried out, wherein the obtained nucleic acid molecule includes both the target sequence and the complementary strand thereof in the sequence.

[2] The method according to [1], wherein a stem part of the hairpin primer has a Tm value higher than a Tm value of the single strand part.

[3] The method according to [1], wherein the synthesized complementary strand sequence performs a template extension reaction in accordance with a reduction in the hairpin primer due to the advance of the reaction.

[4] The method according to [1], further including a step in which the 5' terminal of the hairpin primer is phosphorylated before use and the 5' terminal decomposes the phosphorylated DNA strand after constructing a target nucleic acid molecule.

[5] The method according to [4], wherein the decomposition is performed by using λ exonuclease.

[6] The method according to [4], wherein after the 5' terminal decomposes the phosphorylated DNA strand, the extension reaction of self-annealing from the 3' terminal of the complementary strand thereof through the hairpin structure is performed.

[7] The method according to [1], further including a step in which an adapter having a hairpin loop structure is connected to the product and a strand displacement reaction is performed to extend the nucleic acid molecule.

[8] The method according to [6], wherein an adapter having a hairpin loop structure is connected to the product and a strand displacement reaction is performed to extend the nucleic acid molecule.

[9] The method according to [1], wherein a terminal formed from the primer in a pair is immobilized and the extension reaction is performed after the complementary strand DNA is dissociated.

[10] The method according to [7] or [8], wherein a loop structure part of the adapter includes an extension reaction inhibitor molecule.

[11] The method according to [1], wherein the primer in a pair has a chimeric structure of DNA and RNA, and the method further includes a step in which the RNA is decomposed after the extension reaction.

[12] A nucleic acid base sequencing method including analyzing the base sequence of the nucleic acid molecule obtained by the method according to [1] by a nanopore sequencer.

[13] The method according to [12], wherein in a sequencing step, correction of a detector is performed on the basis of a signal obtained from a known base sequence included in the nucleic acid molecule.

[14] The method according to [12], wherein in a sequencing step, analysis is performed on the basis of a signal obtained from a known base sequence included in the nucleic acid molecule.

[15] The method according to [12], wherein a speed of a reaction product passing through a nanopore is controlled by using a reaction product having a double strand formed therein.

[16] The method according to [1], wherein the hairpin primer has a random sequence.

[17] The method according to [16], wherein the hairpin primer has the types of random sequence equal to or more than the number of mutations of the target sequence.

The present description includes part or all of the contents as described in the description and/or drawings of the International Application PCT/JP2015/055529, which is a priority document of the present application.

Advantageous Effects of Invention

The method for constructing a nucleic acid molecule of the present invention has the following effects.

When the nucleic acid molecule constructed by the method of the present invention is sequenced, the target sequence is not merely interrogated once but is interrogated in plural times by a single-stranded nucleic acid (single molecule) in which the target sequence and complementary strand sequences synthesized by using the sequence itself as a template are connected. This enables highly precise analysis to be performed when a target sequence of nucleic acid is interrogated. More specifically, by repeatedly interrogating those in which only the sequence of one of strands is synthesized with a template without complementary strand sequence information on a genomic structure in the single molecule, it is possible to recognize whether a base difference is caused by a mutation or a base difference is caused by a sequence error and to analyze the sequence of nucleic acid with high precision.

The high degree of determination precision of the base sequence of the single molecule enables a mutation derived from an abnormal cell which is slightly included in a genomic DNA derived from a large amount of normal cell to be detected. For example, in a case where DNA having a mutation derived from a cancer cell which is slightly included in blood is intended to be detected, DNA is extracted from a certain amount of blood, a nucleic acid molecule including a base sequence site, which is intended to be detected, is amplified by using a polymerase chain reaction (PCR) method or the like, and then abase sequence of the nucleic acid molecule is determined. Thus, whether the mutation is included is analyzed (Couraud S. Clin Cancer Res. 2014 Sep. 1; 20(17): 4613-24).

In the case of analyzing a base sequence of a single-molecular DNA by using a nanopore sequencer, when the degree of determination precision of the base sequence by reading once is 90%, it is difficult to detect DNA having a mutation derived from a cancer cell that is slightly included at about 1% in normal cells, for example. In a case where 1,000 single-molecular DNAs in which only a target sequence is amplified by a PCR method are detected (the base sequences are read) in order to detect about 1% of mutation, each single molecule is detected at a site, which includes no mutation, of the base sequences 1,000 times per one base. Since the degree of determination precision of the base sequences is 90%, incorrect base information is detected "about 100 times" out of 1,000 times (provided that, the frequency of the incorrect detection varies at a certain degree). Since a site, which includes a mutation, of the base sequences includes 10% of incorrect determination and 1% of mutation, of 1,000 times of detection, a base sequence different from predominantly-determined base sequence is determined "about 110 times." Since appearance frequency of a difference between "100 times" and "110 times" of determination different from the predominant determination has a variation (distribution), it is difficult to detect and determine the existence of mutation on the basis of this number of times.

However, in the method of the present invention, even if the degree of determination precision of the base sequence of the single-molecular DNA obtained by one detecting operation is 90%, by performing repeated interrogation in the single molecule using the sequence of only one of strands as a template, for example, the degree of the final determination precision of the single molecule reaches 99.9%, and thus it is possible to detect the mutation DNA which is slightly included. For example, when the degree of the final determination precision is 99.9%, if 1,000 single-molecular DNAs are detected, the appearance frequencies of the bases different from predominant determination at the site including no mutation and the site including a mutation are once and 11 times, respectively. Thus, a difference between the appearance frequencies is large. For this reason, it is easy to detect the existence of mutation on the basis of difference between the appearance frequencies. In this way, the detection of the mutation which is slightly included may lead to early detection of diseases.

In addition, since the method of the present invention performs the polymerase chain reaction using a hairpin primer, it is possible to construct a nucleic acid molecule having a hairpin structure with higher efficiency than that in the case of connecting the hairpin structure by, for example, ligation. Incidentally, error probability in a step of repeating amplification is much lower than sequence error. Thus, it can be said that the degree of precision of the analysis method using the method of the present invention is significantly higher than that of the method of the related art.

BRIEF DESCRIPTION OF DRAWINGS

FIG. 8A is an example illustrating the nucleic acid molecule constructing step in the method of the present invention.

FIG. 8B is an example illustrating the nucleic acid molecule constructing step in the method of the present invention.

FIG. 8C is an example illustrating the nucleic acid molecule constructing step in the method of the present invention.

FIG. 9 shows a result of comparing target sequences.

DESCRIPTION OF EMBODIMENTS

Hereinafter, a method of the present invention will be described in more detail by means of drawings.

The present invention relates to a method for constructing a nucleic acid molecule for nucleic acid sequencing by means of a nanopore sequencer. More specifically, the present invention relates to a method for constructing a single-stranded nucleic acid molecule for nucleic acid sequencing by means of a nanopore sequencer, the method including: a step in which at least one hairpin primer including a single-stranded region at the 3' terminal and a primer in a pair with the hairpin primer are used to synthesize a complementary strand of a template DNA including a target sequence; and a step in which the synthesized complementary strand forms a hairpin structure inside a molecule and a template extension reaction is carried out, in which the obtained nucleic acid molecule includes both the target sequence and the complementary strand thereof in the sequence.

Incidentally, in the case of describing the method of the present invention, the term "target sequence" means only the sequence of a strand on one side throughout the description in the present description in the case of a double-stranded nucleic acid molecule, and the complementary strand of the "target sequence" in a case where a target nucleic acid molecule forms a double strand is not described as the "target sequence." In a case where a complementary strand is formed on the basis of the "target sequence" in the constructing method of the present invention, the complementary strand may be described as the "target sequence" or "target sequence information" in some cases.

The nanopore sequencer is a known technique, and for example, an apparatus described in WO 2013/021815 A1 can be suitably used.

Figure 1:
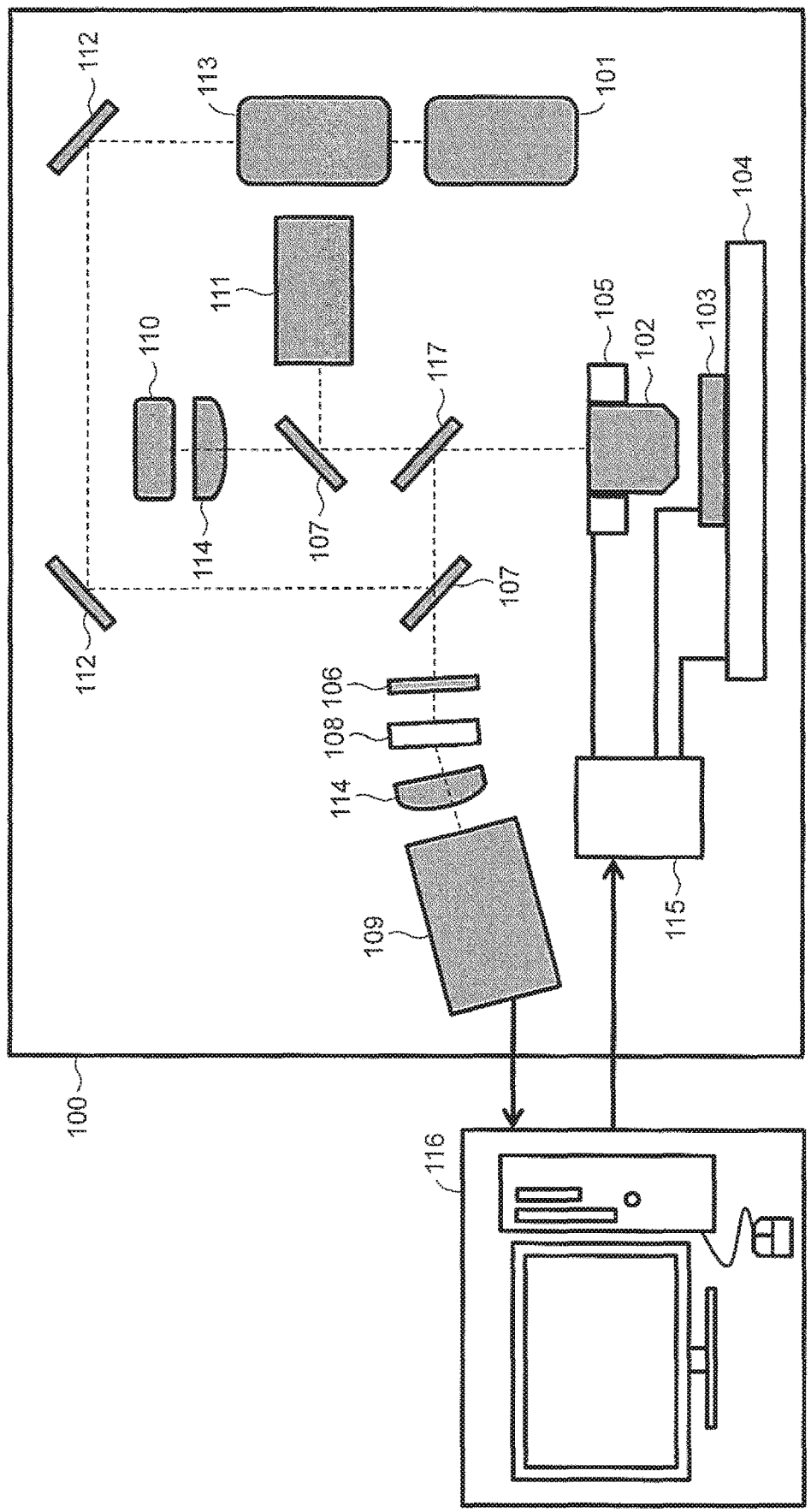
FIG. 1 is an exemplary construction diagram of a nanopore Raman DNA sequencer that can be used in a method of the present invention.

In FIG. 1, a method will be described which uses an apparatus 100 detecting a Raman spectrum after a nucleic acid is caused to enter a nanopore having an inner diameter of about 2 nm and excitation light applied to the nanopore and Raman scattered light of a biopolymer (for example, DNA) passing through the nanopore by an electrically conductive thin film present near the nanopore are amplified.

Herein, a nanopore sequencer detecting a Raman spectrum is described as an example, but the method is applicable to entire technique for analyzing a single-stranded single molecule. For example, the method is a method for constructing a nucleic acid molecule which is also applicable to a DNA sequencer detecting a blockade current or a tunnel current at the time of passing through the nanopore or a nanopore DNA sequencer detecting fluorescence.

In FIG. 1, the configuration and the operation of the apparatus will be described as an example illustrating a case where the apparatus is applied to observation of Raman light using an upright microscope as a basic configuration. The configuration of the apparatus is not limited particularly to the basic configuration of the upright microscope, but it is possible to employ a configuration in which a signal of a sample can be detected with irradiation light, such as a microscope using an inverted microscope as a basic configuration.

The light source applies external light (excitation light) of a wavelength such that fluorescence or Raman scattered light can be produced. A light source 101 well known in the present technical field can be used. For example, as the light source, a semiconductor laser, a krypton (Kr) ion laser, a neodymium (Nd) laser, an argon (Ar) ion laser, a YAG laser, a nitrogen laser, a sapphire laser, or the like can be used, although not exclusively.

When the external light from the light source is applied to a plurality of nanopores, a multiple irradiation mechanism 113 is used. The multiple irradiation mechanism 113 is not limited, but a microlens array, a diffraction grating type beam splitter, a liquid crystal on silicon (LCOS), or the like may be used. The plurality of external light beams are applied to the nanopores by using these.

It is preferable to use a confocal lens and an objective lens 102 in combination with the light source in order to apply the external light from the light source to a microscope observation container and to converge the external light on the microscope observation container. A microscope observation container 103 is installed on an XY stage 104 and the position on the horizontal plane is adjusted by the XY stage. Regarding the position in the vertical direction, adjustment is performed by a Z-axis adjustment mechanism 105 such that a sample to be measured is positioned in a region in which light is condensed with the objective lens. The Z-axis adjustment mechanism may be held by the XY stage according to circumstances. Adjustment may be precisely performed by using a 0-axis stage or a gonio-stage in addition to these stages as a positioning means. These positioning means are controlled by a drive controller 115 and are operated by a user through a computer 116.

Further, as the apparatus configuration, a filter 106 such as a notch filter, a short pass filter, or a long pass filter, a beam splitter 107, a diffraction grating 108, and the like, which are appropriate for a measurement target such as a measurement wavelength region may be combined. In addition, a mirror 112, a pinhole, a lens 114, and a near-infrared (NIR) mirror 117 may be used according to the needs of optical component disposition. The apparatus configuration for detecting such fluorescence or Raman scattered light is well known in the present technical field, and a person skilled in the art can suitably select a preferred constituent element. Any spectroscopic detector can be used as a detector as long as it is a detector 109 that can detect fluorescence or Raman scattered light. In addition, one or a plurality of one-dimensional or two-dimensional detectors can be used according to the number of samples and the disposition of samples in the microscope observation container to be used. Examples of such a spectroscopic detector include a charge-coupled device (CCD), an electron multiplying CCD image sensor, a complementary metal-oxide-semiconductor (CMOS) image sensor, and an image sensor using other high-sensitivity element (avalanche photodiode or the like). The detector preferably has a photomultiplication mechanism, for example, an image intensifier in order to prevent a reduction in sensitivity with speed-up of detection. In addition, the detector preferably includes a large-capacity memory capable of directly recording image information of Raman scattered light or the like, and thus high-speed analysis without intermediary devices such as a cable, a board, and a computer can be performed. For example, the analysis apparatus of the present invention may further include a frame buffer memory for recording measurement values from the detector. In addition, the analysis apparatus of the present invention may be connected to the computer 116 for digitizing measurement values from the detector, performing arithmetic processing thereon, and outputting the measurement values.

Further, the apparatus may have a function capable of observing a bright-field image as well as detecting Raman scattered light or fluorescence. For doing this, as illustrated in FIG. 1, an LED 110 is used as a bright-field irradiation light source and a two-dimensional detector 111 is used as a bright-field imaging element. Examples of the two-dimensional detector include a CCD or EMCCD image sensor and a CMOS image sensor.

Figure 2:
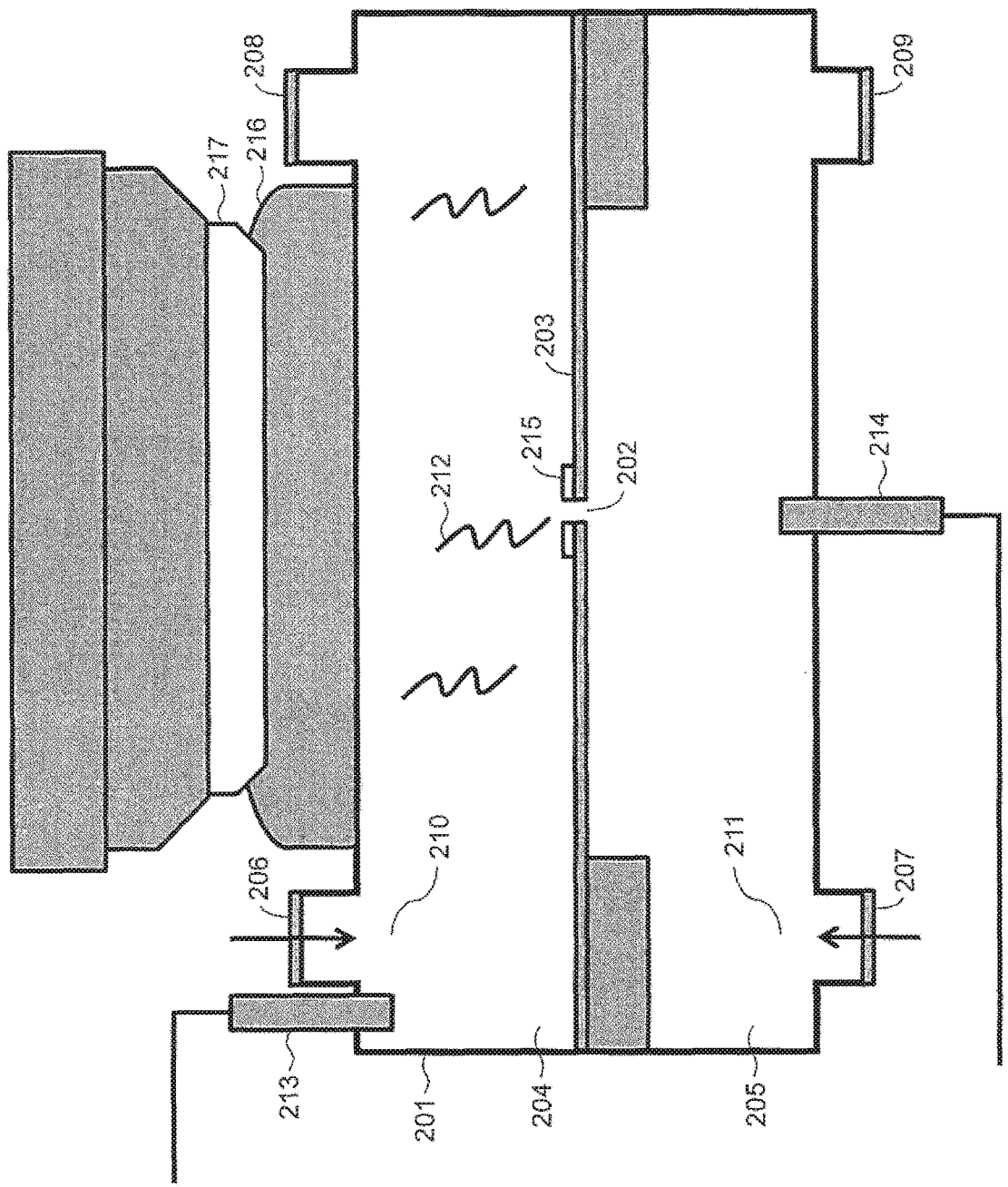
FIG. 2 is an exemplary cross-sectional view of a detecting unit and an observation container of the nanopore Raman DNA sequencer that can be used in the method of the present invention.

FIG. 2 illustrates a cross-sectional configuration of a nanopore substrate and an observation container having the nanopore substrate disposed therein. An observation container 201 is configured by two closed spaces separated by a substrate 203 having a nanopore 202 (nanopore substrate), that is, by a sample introduction section 204 and a sample outflow section 205. Herein, the sample introduction section 204 and the sample outflow section 205 are communicated with each other by the nanopore 202. A molecule is input to the observation container 201 after construction of a nucleic acid molecule repeatedly including a target sequence which is constructed by the method of the present invention described later. Alternatively, a nucleic acid molecule may be directly constructed in the observation container.

The observation container includes a chamber part and the substrate 203 disposed therein. The substrate 203 includes a base material, a thin film formed to face the base material, and the nanopore 202 provided in the thin film and communicating between the sample (nucleic acid molecule) introduction section 204 and the sample outflow section 205, and the substrate is disposed between the sample introduction section 204 and the sample outflow section 205 in the chamber. The substrate 203 may have an insulating layer. The substrate 203 is preferably a solid substrate.

The substrate 203 can be formed from an electrically insulating material, for example, an inorganic material and an organic material (including a polymer material). Examples of the electrically insulating material forming the substrate 203 include silicon, silicon compound, glass, quartz, polydimethylsiloxane (PDMS), polytetrafluoroethylene (PTFE), polystyrene, and polypropylene. Examples of the silicon compound include silicon oxynitride such as silicon nitride, silicon oxide, and silicon carbide. In particular, abase (base material) configuring a support portion of the substrate 203 can be produced from any of these materials, but for example, silicon or the silicon compound may be used.

The size and the thickness of the substrate 203 are not particularly limited as long as the nanopore 202 can be provided thereon. The substrate 203 can be produced by a method well known in the present technical field, or a commercially available product can also be used. For example, the substrate 203 can be produced by using a technique such as photolithography, electron lithography, etching, laser abrasion, injection molding, casting, molecular beam epitaxy, chemical vapor deposition (CVD), dielectric breakdown, electron beam, or focused ion beam. The substrate 203 may be coated in order to avoid adsorption of molecules other than the target molecule to the surface.

The substrate 203 has at least one nanopore 202. Specifically, the nanopore 202 is provided on a thin film, but the nanopore 202 may be provided simultaneously on the base (base material) and an insulating body depending on the circumstances. In the present invention, each of "nanopore" and "pore" is a hole of a nanometer (nm) size (that is, a diameter of 1 nm or more but less than 1 μm) that allows the sample introduction section 204 and the sample outflow section 205 to be communicated with each other through the substrate 203.

The substrate 203 preferably has a thin film for providing the nanopore 202. That is, the provision of the thin film on the substrate made of a suitable material and having a suitable thickness for forming a nanosize hole enables the nanopore 202 to be easily and efficiently formed on the substrate 203. From the viewpoint of forming the nanopore, the material of the thin film is, for example, preferably silicon oxide ($SiO_2$), silicon nitride (SiN), silicon oxynitride (SiON), metal oxide, metal silicate, or the like. In addition, the thin film (and the entire substrate in some cases) may be substantially transparent. Herein, "substantially transparent"

means that about 50% or more, preferably 80% or more of external light can be transmitted. Furthermore, the thin film may be a single layer or a multilayer. The thickness of the thin film is 1 nm to 200 nm, preferably 1 nm to 50 nm, and more preferably 1 nm to 20 nm. The thin film can be formed on the substrate 203 by a technique well known in the present technical field, for example, low-pressure chemical vapor deposition (LPCVD).

It is also preferable to provide an insulating layer on the thin film. The thickness of the insulating layer is preferably 5 nm to 50 nm. Any insulating body materials can be used for the insulating layer, but it is preferable to use silicon or a silicon compound (such as silicon nitride or silicon oxide). In the present invention, an "opening" of the nanopore or pore denotes an opening circle of the nanopore or pore at a portion of which the nanopore or pore is in contact with a sample solution. At the time of analysis of a biopolymer, a biopolymer or an ion in the sample solution enters the nanopore through the opening on one side and exits the nanopore through an opening on the same side or on the opposite side.

A suitable size for the nanopore 202 can be selected according to the type of the biopolymer to be analyzed. The nanopore may have a uniform diameter, but may have a different diameter depending on portions. The nanopore may be connected to a pore having a diameter of 1 μm or more. It is preferable that the minimum diameter portion, that is, the smallest diameter of the nanopore provided in the thin film of the substrate 203 is 100 nm or less, for example, 1 nm to 100 nm, preferably 1 nm to 50 nm, for example, 1 nm to 10 nm, specifically 1 nm or more but 5 nm or less, and 3 nm or more but 5 nm or less.

The diameter of an ssDNA (single-stranded DNA) is about 1.5 nm, and a suitable range of the nanopore diameter for analyzing an ssDNA is about 1.5 nm to 10 nm and preferably about 1.5 nm to 2.5 nm. The diameter of a dsDNA (double-stranded DNA) is about 2.6 nm, and a suitable range of the nanopore diameter for analyzing a dsDNA is about 3 nm to 10 nm and preferably about 3 nm to 5 nm. Also in the case of analyzing a different biopolymer, for example, a protein, polypeptide, a sugar chain, or the like, a nanopore diameter according to the outer diameter size of the biopolymer can be selected.

The depth (length) of the nanopore 202 can be adjusted by adjusting the thickness of the substrate 203 or the thickness of the thin film of the substrate 203. It is preferable to set the depth of the nanopore 202 to a monomer unit constituting the biopolymer to be analyzed. For example, in the case of selecting a nucleic acid as a biopolymer, it is preferable to set the depth of the nanopore 202 to be equal to or less than a size corresponding to one base, for example, about 0.3 nm or less. The shape of the nanopore 202 is basically circular, but can alternatively be made elliptical or polygonal.

At least one nanopore 202 can be provided in the substrate 203, and in the case of providing a plurality of nanopores 202, it is preferable to regularly arrange the nanopores. The nanopore 202 can be formed by a method well known in the present technical field, for example, by applying an electron beam from a transmission electron microscope (TEM) and by using a nanolithography technique, an ion beam lithography technique, or the like.

The chamber part has the sample introduction section 204, the sample outflow section 205, the substrate 203, a voltage applying means, electrodes 213 and 214 for allowing a sample 212 to pass through a nanopore 202, and the like. In a preferred example, the chamber part has the sample introduction section 204, the sample outflow section 205, the first electrode 213 provided in the sample introduction section 204, the second electrode 214 provided in the sample outflow section 205, a voltage applying means with respect to the first and second electrodes, and the like. An ammeter may be disposed between the first electrode 213 provided in the sample introduction section 204 and the second electrode 214 provided in the sample outflow section 205. A current between the first electrode 213 and the second electrode 214 may be set appropriately from the standpoint of determining the speed of the transfer of the sample 212 through the nanopore and is preferably, but not limited to, about 100 mV to 300 mV for DNA in a case where ionic liquid not containing the sample 212 is used, for example.

The electrodes 213 and 214 can be produced from a metal such as platinum group metal such as platinum, palladium, rhodium, or ruthenium; gold, silver, copper, aluminum, or nickel; graphite, for example, graphene (may be monolayered or multilayered), tungsten, tantalum, or the like.

The nucleic acid molecule passing through the nanopore 202 by applying a voltage emits Raman light by excitation light, but an electrically conductive thin film 215 may be prepared near the nanopore to generate a near field and then intensify the near field. The electrically conductive thin film 215 disposed near the nanopore is formed in a planar shape as clearly seen from the definition of the thin film. The thickness of the electrically conductive thin film 215 is set to 0.1 nm to 10 nm, preferably 0.1 nm to 7 nm according to the material to be employed. As the thickness of the electrically conductive thin film 215 is decreased, a near field to be generated can be restricted to enable analysis at a high resolution and high sensitivity. In addition, the size of the electrically conductive thin film 215 is not particularly limited, and a suitable size for the electrically conductive thin film can be selected according to the sizes of the solid substrate 203 and the nanopore 202 to be used, a wavelength of excitation light to be used, and the like. Incidentally, when the electrically conductive thin film 215 does not have a planar shape and there is bending or the like, a near field is induced in a bending portion thereof to leak light energy so that Raman scattered light is generated in a place other than the target. That is, background light is increased and S/N is decreased. For this reason, the electrically conductive thin film 215 preferably has a planar shape; in other words, the cross-sectional shape is preferably linear without bending. Forming the electrically conductive thin film 215 in a planar shape is not only effective at reducing the background light and increasing the S/N ratio but also preferable from the viewpoint of uniformity of the thin film, reproducibility in production, and the like.

The sample introduction section 204 and the sample outflow section 205 are to be filled with liquids 210 and 211 introduced through inflow paths 206 and 207 connected to both sections respectively. The liquids 210 and 211 flow out from outflow paths 208 and 209 connected to the sample introduction section 204 and the sample outflow section 205. The inflow paths 206 and 207 may be provided at a position where the inflow paths face each other with the substrate interposed therebetween, but are not limited thereto. The outflow paths 208 and 209 may be provided at a position where the outflow paths face each other with the substrate interposed therebetween, but are not limited thereto.

The liquid 210 is preferably a sample solution containing the sample 212 to be analyzed. The liquid 210 contains an ion that becomes a charge carrier preferably in a large amount (hereinafter, referred to as ionic liquid). The liquid 210 preferably contains only ionic liquid except for the sample. An aqueous solution in which a highly-ionized electrolyte is dissolved is preferable as the ionic liquid, and a solution of salts, for example, an aqueous solution of potassium chloride, can be suitably used. The sample 212 is preferably one to be charged in the ionic liquid. The sample 212 is typically a nucleic acid molecule.

The electrodes 213 and 214 disposed to face each other with the nanopore 202 interposed therebetween are provided in the sample introduction section 204 and the sample outflow section 205. In the present embodiment, the chamber part also includes a voltage applying means with respect to the electrodes 213 and 214. When the voltage is applied, the sample 212 having a charge passes through the nanopore 202 from the sample introduction section 204 to move to the sample outflow section 205. When the sample 212 passes through the nanopore 202 irradiated with excitation light, a Raman scattering spectrum enhanced by the electrically conductive thin film 215 is analyzed by effectively condensing Raman light with a liquid immersion medium 216 and then allowing the Raman light to reach a detector 109 through an objective lens 217.

In FIG. 2, the sample introduction section is set as the upper part and the sample outflow section is set as the lower part; however, the sample introduction section may be set as the lower part, the sample outflow section may be set as the upper part, and then the sample passing through the nanopore may be detected.

Hereinafter, the method of the present invention will be described in detail by means of Examples, but the method of the present invention is not intended to be limited to the following Examples.

Example 1

Figure 3:
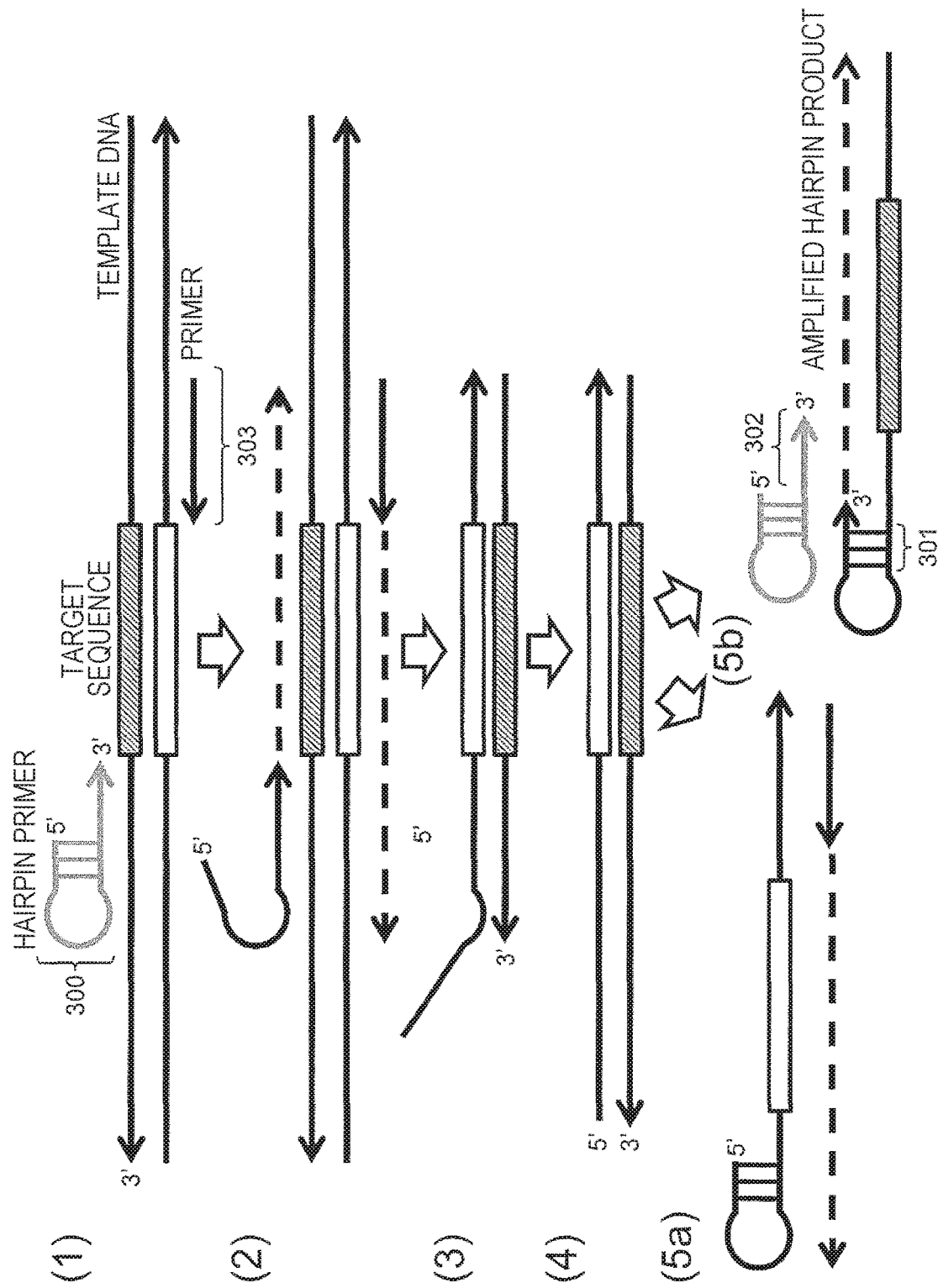
FIG. 3 is an example illustrating a nucleic acid molecule constructing step in the method of the present invention.

FIG. 3 illustrates an embodiment of the method of the present invention. The method for constructing a nucleic acid molecule of the present invention has a feature that a target sequence of nucleic acid as a target is amplified and the target sequence is repeated to construct a single strand (single molecule).

As illustrated in FIG. 3 (1), at least one of a pair of primers to be prepared is designated as a primer 300 having a hairpin structure. The 3' terminal of the primer 300 has a primer sequence structure of the single-stranded region having a sequence complementary to the template DNA sequence including the target sequence and is configured to protrude from the stem part. In this case, the primer 300 for amplification of the target sequence is a hairpin primer, and the primer 303 for amplification of the complementary strand of the target sequence may be a hairpin primer or a primer having no hairpin structure. Alternatively, a primer 303 can be used for amplification of the target sequence and the hairpin primer 300 can be used for amplification of the complementary strand of the target sequence. The method of the present invention in which any one of sequences of the double-stranded nucleic acid is analyzed as a target sequence can also use any aspects described above in accordance with the embodiment. In any cases, the primer 303 in comparison with the hairpin primer 300 is referred to as the "primer in a pair" in this description.

For the template DNA, DNA derived from a sample itself including a target sequence can be used without any changes, but a target sequence can be connected to a sequence synthesized to include a sequence capable of forming a strand completely complementary to the hairpin primer so that the target sequence can be more preferably used in the method of the present invention.

A primer with a hairpin structure having a loop part and a stem part is known, and as a sequence example thereof, there is mentioned a sequence example having a hairpin structure presented in the following Table 1 from I. A. Nazarenko. et al. 2516-2521 Nucleic Acids Research, 1997, Vol. 25, No. 12. A person skilled in the art can appropriately design and prepare a hairpin primer suitable for amplification of a template DNA to be amplified including a target sequence as long as the template DNA is specified.

TABLE 1

| Name | Sequence |
| --- | --- |
| Sequence Example 1 | 5'-ACCTTCTACCCTCAGAAGGTGACCAAGTTCAT-3' (SEQ ID No: 1) |
| Sequence Example 2 | 5'-ACCTTCTATACCCTCAGAAGGTGACCAAGTTCAT-3' (SEQ ID No: 2) |
| Sequence Example 3 | 5'-CACCTTCACCCTCAGAAGGTGACCAAGTTCAT-3' (SEQ ID No: 3) |

As illustrated in FIG. 3, the primer 300 having a hairpin structure is denatured and then annealed to a target sequence of a target nucleic acid (for example, a human genome).

As an example, in Step (1) of FIG. 3, a solution containing a target nucleic acid, a primer set interposing a target sequence (one in which one or both terminals are the aforementioned hairpin primer (s) 300), a polymerase, and a salt composition solution appropriate to the polymerase are prepared as a reaction solution mixture. A DNA polymerase to be used is not limited, and for example, it is possible to use one which is a polymerase represented by a Taq DNA polymerase and isolated from thermophilic bacteria and is classified into family A (PolI type), or one which is a polymerase represented by a KOD DNA polymerase and isolated from hyperthermophilic archaebacterium and is classified into family B (α type). In addition, as a strand displacement type DNA polymerase that catalyzes the complementary strand synthesis reaction, a Bst DNA polymerase, a Bca (exo-) DNA polymerase, a Klenow fragment of DNA polymerase I, a Φ29 phage DNA polymerase, a Vent DNA polymerase, a Vent (Exo-) DNA polymerase (excluding exonuclease activity from a Vent DNA polymerase), a DeepVent DNA polymerase, a DeepVent (Exo-) DNA polymerase (excluding exonuclease activity from a DeepVent DNA polymerase), a MS-2 phage DNA polymerase, a Z-Taq DNA polymerase (produced by Takara Bio Inc.), and the like are generally known and can be suitably used.

Further, those which have required catalytic property of the DNA polymerase and have only a part of functions such as a structure, or various mutants whose catalytic property, stability, or heat resistance has been modified by amino acid mutations may be used. Various DNA polymerase mutants can be used in the present invention as long as they have the activity of sequence-dependent complementary strand synthesis, the strand displacement activity, and the like, and DNA polymerase mutants are not limited to the above-described examples.

Since the method of the present invention is a technique of enhancing the degree of reading precision of the sequencer by reading the sequence produced by the synthesis in plural times, a polymerase having a high synthesis precision is preferable. For example, the degree of synthesis precision of enzymes with a high synthesis precision such as PrimeSTAR (registered trademark) Max and PrimeSTAR (registered trademark) HS (produced by Takara Bio Inc.) is known to be 99.995% or more. They have a sufficient degree of precision for detecting 1 to 0.1% of mutation that the synthesis mistake at the amplification stage does not influence mutation detection.

In Step (2) of FIG. 3, the mixtures of (1) are heated up to an appropriate denaturation temperature, each primer is annealed to the target nucleic acid, and then the extension reaction is performed (Step (3)). The extended double-stranded amplified product is dissociated under the denaturation condition, then annealed again to each primer, and extended. This step is repeatedly performed. Herein, the whole loop part of the hairpin primer also forms a base pair in the extended double-stranded amplified product and is included (Step (4)).

As illustrated in (5b), at this time, since the extended single-stranded nucleic acid includes the sequence of the hairpin primer in the molecule, it is possible to form a single-stranded nucleic acid having a hairpin structure in the molecule by annealing. This reaction and a reaction of forming a new complementary strand by intermolecular annealing with the unreacted hairpin primer 300 compete against each other. Herein, in order to preferentially obtain a single-stranded nucleic acid repeatedly including a target sequence as illustrated in (5b) and having a hairpin structure, it is preferable that the annealing of the complementary strand sequence part 301 (stem part) forming a hairpin structure occurs on the 3' terminal rather than the annealing with the unreacted hairpin primer 300. For doing this, for example, when the temperature (Tm value) necessary for annealing the complementary strand sequence part 302 (single strand part) in the hairpin primer of the hairpin primer 300 in which annealing operations compete against each other is designed to be lower than the Tm value of the complementary strand sequence part 301 (stem part) forming a hairpin structure and a temperature gradient is provided such that the temperature is lowered from the denaturation step to the annealing and extension step, the complementary strand sequence part 301 (stem part) is preferentially annealed, and thus it is possible to preferentially obtain a single-stranded nucleic acid having a hairpin structure in which the target sequence is repeated. That is, in this case, the stem part of the hairpin primer has a Tm value higher than the Tm value of the single strand part. The Tm (melting temperature) value in this context is described as a value with respect to the partial sequence in the primer.

For example, in the case of designing sequences such that the Tm value of the single strand part of the hairpin primer is set to 60° C., when the Tm value of the stem part is set to 70° C., the complementary strand sequence part 301 is preferentially annealed and a single-stranded nucleic acid having a hairpin structure in which the target sequence is repeated can be preferentially obtained.

In general, the aspect of the double-stranded DNA changes at the Tm value±5° C. If a difference between the Tm values is set with a margin, a difference between the Tm values of the single strand part and the stem part may be set to 15° C. or higher. However, since setting of the Tm values to have an extreme difference also influences the reaction efficiency of amplification, a temperature difference may be set to 15° C. or lower and more preferably about 10° C. Therefore, as an embodiment of the method of the present invention, the stem part of the hairpin primer 300 is set to have a Tm value higher than the Tm value of the single strand part of the hairpin primer 300 by 5° C. or higher, 10° C. or higher, or 15° C. or higher. Alternatively, the stem part of the hairpin primer 300 is set to have a Tm value higher than the Tm value of the single strand part of the hairpin primer 300 by about 5° C., about 6° C., about 7° C., about 8° C., about 9° C., about 10° C., about 11° C., about 12° C., about 13° C., about 14° C., or about 15° C.

Further, when betaine (N,N,N-trimethylglycine) that adjusts the melting temperature of DNA is used, the aspect of the double-stranded DNA can be changed in a narrower temperature range (William A. Rees et al., Biochemistry 1993, 32, 137-144) and thus betaine may be added to the reaction solution.

The Tm value or the aspect of the double-stranded DNA at each temperature varies depending on conditions such as pH and salt concentration and is a value dependent also on the base sequence and length, but the Tm value under certain conditions can be calculated on the basis of the length of the base sequence, the GC content, and the like. A person skilled in the art can appropriately set Tm values of each part in design of the primer to design and prepare an optimal primer, and can also suitably design reaction temperature.

Alternatively, since the concentration of the hairpin primer 300 decreases as the reaction cycle proceeds without performing the aforementioned step, the concentration of the primer 300 may be appropriately adjusted by depletion of the primer 300 such that the complementary strand sequence part 301 is preferentially annealed. In this case, the synthesized complementary strand sequence performs the template extension reaction in accordance with a reduction in the hairpin primer due to the advance of the reaction.

More specifically, for performing the above-described reaction, a hairpin primer having a sequence structure as presented in Table 1, polymerase, and a composition at the time of preparing 100 µl of salt composition solution are prepared, for example, as follows:
20 mM Tris-HCl (pH 8.5)
50 mM KCl
2 mM $MgCl_2$
200 µM each dNTP
5U $Pfu^{exo}$-DNA polymerase (polymerase not having 3'-5' exonuclease activity).

Then, the synthesis reaction is performed under the following temperature conditions.

A high-order structure of a hairpin and a target nucleic acid (for example, human genome) is detangled by heating at 94° C. for 5 min. Thereafter, a temperature cycle of 95° C. for 30 sec, 60° C. for 45 sec, and 72° C. for 90 sec is repeated, for example, 20 to 40 times, and then the extension reaction is performed at 72° C. for 5 min. The time and the temperature in the temperature cycle are not limited to the reaction conditions described herein. The temperature, the time, the cycle, and the like may be changed according to a target sequence, the sequence of a primer, a desired product, and the like.

By the process of FIG. 3 in which these steps are repeated, it is possible to obtain a single-stranded nucleic acid having a hairpin structure in which a target sequence is repeated as illustrated in (5b), and thus it is possible to rapidly construct a sample before base sequencing.

Incidentally, in FIG. 3, one of the primers in a pair is designated as the hairpin primer 300, but the same reaction step may be performed by using the primer of the primers in a pair that both have a hairpin structure. The time for constructing a nucleic acid molecule depends on the temperature, the reaction time, the cycle, and the thermostat (thermal-cycler) performance in the synthesis reaction, but the reaction illustrated in FIG. 3 is terminated within about 30 min to 90 min. The reaction solution contains an unreacted primer or the like. However, the unreacted primer is removed by using a spin column filled with a gel filtration resin CHROMA SPIN Column (produced by Takara Bio Inc.) for about 10 min, only the synthesized nucleic acid molecule in which the target sequence is repeated is extracted, and then the process may be allowed to proceed to the step of base sequencing.

Since the product obtained by the method of the present invention has a complementary strand sequence, one forming a double strand (5a) is mixed with the single-stranded nucleic acid molecule (5b) having a hairpin structure. In order to analyze a sequence by a sequencer using a nanopore (for example, a diameter of 2 nm or less) that allows a single-stranded DNA to pass therethrough and detects a sequence per one base, it is not preferable that a double-stranded nucleic acid molecule exists at the time point of sequence analysis. Therefore, for example, in the synthesis step illustrated in FIG. 3, one of two primers to be used may be set to the primer 303 not having a hairpin structure, and then the sequence of the primer 303 may be set to an AT-rich sequence in which a complementary strand sequence is easily dissociated. Alternatively, a complementary strand sequence is dissociated by heat or alkali when the product passes through the nanopore, and thus the nanopore may be configured to easily allow the product to pass therethrough as a single-stranded DNA.

Alternatively, a hybrid chimeric primer configured by DNA-RNA is used as the primer 303, an RNA sequence is prepared on the 5' terminal, and then the reaction illustrated in FIG. 3 can also be performed. In this case, the RNA forming the DNA-RNA hybrid double strand is cut by using an RNase H enzyme or the like, a site in which the terminal of the reaction product becomes a single-stranded DNA is formed, and then the product may easily pass through the nanopore from the site of the single-stranded DNA. When the site of the double-stranded DNA sequence passes through the nanopore from the sequence at the site that becomes the single-stranded DNA, the negatively charged DNA passes through the nanopore and then electrically incorporated to a positive electrode side. The double-stranded DNA is formed by hydrogen bond and the DNA may be incorporated while the hydrogen bond is dissociated. In this case, the speed of the DNA passing through the nanopore is decreased, and thus it is also possible to pass the DNA over sufficient time through the site that becomes a sufficient detection site. That is, the speed of the DNA passing through the nanopore can also be controlled by adjusting the force of the hydrogen bond forming a double strand by heat or alkali or by adjusting the incorporation force.

The method of the present invention synthesizes a complementary strand sequence on the basis of only a target sequence (one DNA strand of one side of a double strand), continuously synthesizes a complementary strand sequence of the synthesized sequence to construct a single-stranded nucleic acid molecule, and then performs detection with a nanopore sequencer by using the single-stranded nucleic acid molecule. Even when a base sequence is difficult to read by the analysis of only one strand of the target sequence, for example, when a signal to be obtained is not certain due to a case where there is a similar signal between bases, or the like, the method can obtain signals from complementary strand sequences each having a different sequence. That is, this represents that since both of original double strand molecules including a mismatch possibility are not read but sequence information of only one strand of the same target sequence is read twice, highly precise analysis of the nucleic acid sequence can be performed by using the information read twice. Although a detecting apparatus (for example, a detector, a lens, or the like) is not an expensive and highly precise apparatus, an apparatus that can obtain a sufficient degree of precision by performing reading in plural times may be used as the detecting apparatus, that is, a load (for example, a functional load) of the apparatus may be reduced. Thus, the method of the present invention also corresponds to a method capable of using an inexpensive or small-sized apparatus as an apparatus for sequencing.

The analysis by the nanopore sequencer can be performed from any of the 5' terminal and the 3' terminal in the case of the single-stranded nucleic acid molecule. In the case of performing nanopore sequencing by using the reaction product produced in the above-described step, when the amplified hairpin product illustrated in FIG. 3 (5b) is intended to be read from the 5' terminal, the sequence information of the primer is first analyzed, and then the target sequence, the hairpin primer sequence, the target sequence (complementary sequence), and the primer sequence (complementary sequence) are analyzed in this order.

Herein, since the base sequence information derived from each primer sequence and the signal information of the base sequences (for example, Raman scattered light and a blockade current value) are already known, which signal (a wavelength, a wave number, or a current value) a peak is obtained from and what order the signal corresponding to each base obtains a peak are known in advance. Thus, correction for detection can be performed in real time. For example, in the case of detecting Raman scattered light, since spectrum information based on known Raman scattered light is sequentially obtained, information obtained from a spectrum peak is not obtainable at a position of an element from which the information is originally obtainable, for example, the position of the detection element may be corrected. When the optical axis is deviated, a spectrum peak is obtained at a position of a detection image element different from the original, and thus correct analysis cannot be carried out. In this regard, by using the matter that a plurality of known Raman spectrum peaks are obtained between start and end of base sequence reading and between target sequences, the wave number and the positional information of the element can be corrected and analyzed by using a plurality of items of known positional information composed of a detection image element position of the plurality of Raman spectrum peaks and a detection image element position of excitation light (not Raman light but reflection light of excitation light) obtained at the initial stage of analysis, element positional information which may be originally detected, and the like.

The plurality of known Raman spectrum peaks obtained from sequence parts can also be used for detection of contamination and carry-over as well as position correction of the element. For example, in the case of analyzing target sequences of a plurality of samples, a sequence of a hairpin part of the hairpin primer 300 to be used in analysis is changed for each sample. Alternatively, by providing a target sequence and a sequence not having a complementary sequence on the 5' terminal of the primer 303 in a pair and changing the sequence for each sample, contamination between samples and carry-over of the analysis sample before analysis can be recognized and analyzed from the read sequence information.

In the case of performing current sensing, correction may be performed by using a current value and a background signal value obtained from each base of each known primer sequence. For example, it is particularly effective in a case where a background signal value varies during measurement. A signal value immediately before a nucleic acid passing is set to a background signal value, and since a current value largely changes when the nucleic acid molecule is incorporated, a current value is measured by subtracting the background signal value obtained before the nucleic acid molecule is incorporated. In a case where a known base sequence aligned with ACGT is sequentially measured, a base may be determined by subtracting a background signal value from the signal intensity of each base and then comparing a signal value obtained in the target sequence part with a reference value when a signal intensity ratio or signal change by a known sequence is designated as a reference value. The correction method is not limited thereto. The method is a method for performing correction or analysis based on a known signal value or signal information obtained from a known sequence, or an actual measurement signal by a known sequence obtained from a known sequence. A person skilled in the art can appropriately modify the method of the present invention on the basis of the above description.

In the above description, the example in which the Raman scattered light is detected to determine the nucleic acid base sequence has been mainly described, but the method of the present invention is not limited thereto. For example, the nucleic acid molecule obtained by the method of the present invention can be used in a nucleic acid sequencing method (US 2011/0229877, US 2011/0177498, or the like) which detects a blockade current at the time of passing through the nanopore, a nucleic acid sequencing method (Japanese Unexamined Patent Application Publication No. 2014-20837) which senses a tunnel current generated at the time of passing through the nanopore, a single-molecular nucleic acid sequencing method (WO 2014111723 A, WO 2014053854 A) which uses a droplet, a nucleic acid sequencing method (Japanese Patent No. 4638043) which detects a single molecule of a fluorescently labelled pyrophosphoric acid [PPi] part discharged from nucleotide triphosphate [NTP] when a polymerase extension product is produced, or the like. Even when the degree of reading precision of the target sequence is low, since a plurality of items of target sequence information are included in the molecule, a highly precise analysis result can be exhibited by analyzing a single molecule, and a load (for example, a functional load) of a detecting apparatus may be reduced.

Example 2

Figure 4:
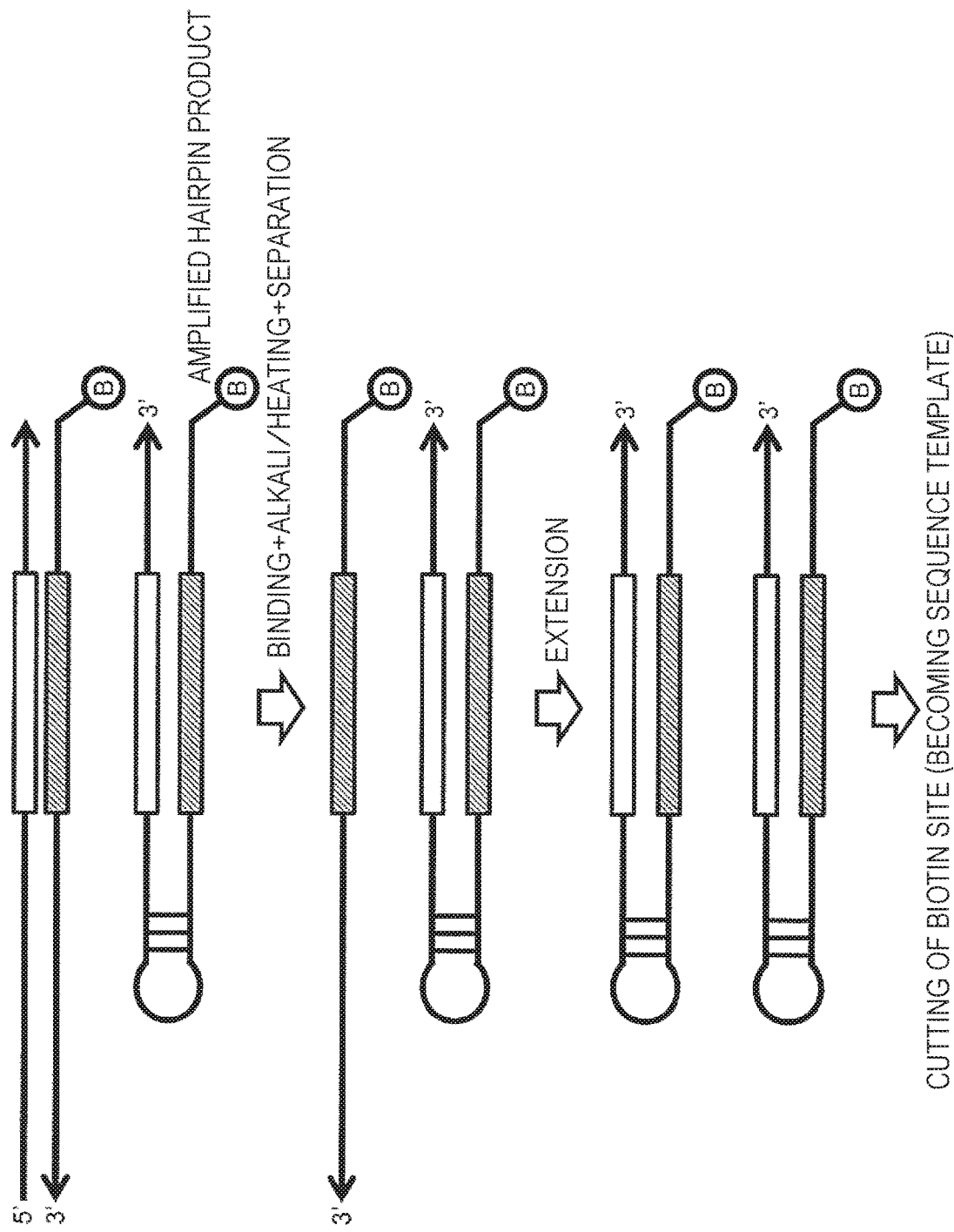
FIG. 4 is an example illustrating the nucleic acid molecule constructing step in the method of the present invention.

In Example 1, the nucleic acid molecule constructed in the case of using the hairpin primer at only one side is constructed such that the molecule illustrated in (4) of FIG. 3 and the molecule illustrated in (5b) of FIG. 3 are constructed in approximately equal proportions. In this Example, a method will be described by which the molecule illustrated in (5b) of FIG. 3 in which the target sequence can be detected twice is not constructed in approximately equal proportion but the total molecule to be constructed is constructed to become a molecule in which the target sequence can be detected twice. FIG. 4 illustrates procedures thereof.

In this Example, a step similar to FIG. 3 is performed before the step illustrated in FIG. 4. The step similar to FIG. 3 is different from the step of FIG. 3 in that the primer 303 in a pair with the hairpin primer 300 is biotinylated and then the amplification step illustrated in FIG. 3 is performed. With the biotinylation of the primer, in order to reduce an amplification failure in the synthesis using a polymerase generated by the steric structure of biotin, a spacer (for example, a base or the like) having about 5 carbon atoms may be contained.

By using the biotinylated primer 300, magnetic beads with streptavidin (for example, Dynabeads (registered trademark) M-280 Streptavidin) is mixed, for example, with 40 µl of the reaction product amplified in the step illustrated in FIG. 3, and the resultant product is incubated at room temperature for 15 min while being suspended so that the amplified product and the magnetic beads are bound to each other.

Thereafter, a magnet is installed outside a reaction container, only the supernatant is removed in a state where magnetic beads are drawn to the magnet side over the reaction container and fixed, and a cleaning operation of adding and suspending a cleaning solution, drawing by the magnet, and removing the supernatant is performed. At the time of the cleaning operation, when the cleaning solution is set to 60° C. or higher or 95° C. or higher, DNA strands present in the complementary strands of the DNA strands bound to the magnetic beads are washed off along with dissociation of the double-stranded DNA, and the DNA strand bound to the magnetic bead, that is, only a molecule which is extended from a biotinylated primer can be isolated. Alternatively, the same effect is obtained also by cleaning with an alkali solution while dissociation of the double-stranded DNA is performed.

As the method for isolating only DNA strands bound to the magnetic beads, a method of performing treatment by cleaning under high temperature and cleaning with an alkali solution is described, but the isolating method is not limited thereto. The isolating method may be a method of dissociating the state of binding the complementary strand sequence of the DNA strand and isolating only the molecule extended by the biotinylated primer.

A molecule in which the target sequence can be detected twice in the total molecule is constructed by using this isolated DNA strand. For example, a solution having the following composition at the time of preparing 100 µl of reaction solution is added to the isolated DNA strand.
20 mM Tris-HCl (pH 8.5)
50 mM KCl
2 mM $MgCl_2$
200 µM each dNTP
5U $Pfu^{exo}$-DNA polymerase (polymerase not having 3'-5' exonuclease activity)
Then, the reaction is performed under the following temperature conditions.

A high-order structure is detangled by heating at 94° C. for 5 min. Thereafter, a hairpin structure is constructed by annealing a sequence site having a complementary strand of the 3' terminal at 95° C. for 30 sec and at 60° C. for 45 sec, and then the extension reaction is performed by heating at 72° C. for 90 sec or longer.

As a result, as illustrated in FIG. 4, it is possible to obtain only a single-stranded nucleic acid having a hairpin structure repeatedly containing target sequence information. Incidentally, the reaction conditions are not limited to the above-described reaction conditions, and the temperature, the time, the cycle, and the like may be changed according to a target sequence or a sequence of a primer. Further, there is no description on a purification step of removing a salt or an enzyme between reaction processes of respective steps, but if necessary, the purification step may be performed according to circumstances.

When the nanopore sequencing is performed, in a case where the sequencing efficiency is lowered by the bound magnetic bead, the magnetic bead may be separated from the nucleic acid molecule. For example, a spacer region provided between the primer and biotin may be cut. As a cutting method, for example, a restriction enzyme cleavage sequence is allowed to be contained in advance in the base sequence of the spacer region and can be cut before sequencing. According to this, a product obtained by separating the DNA strand and the magnetic bead from each other can be used as a sample and then subjected to nanopore sequencing.

Example 3

Figure 5:
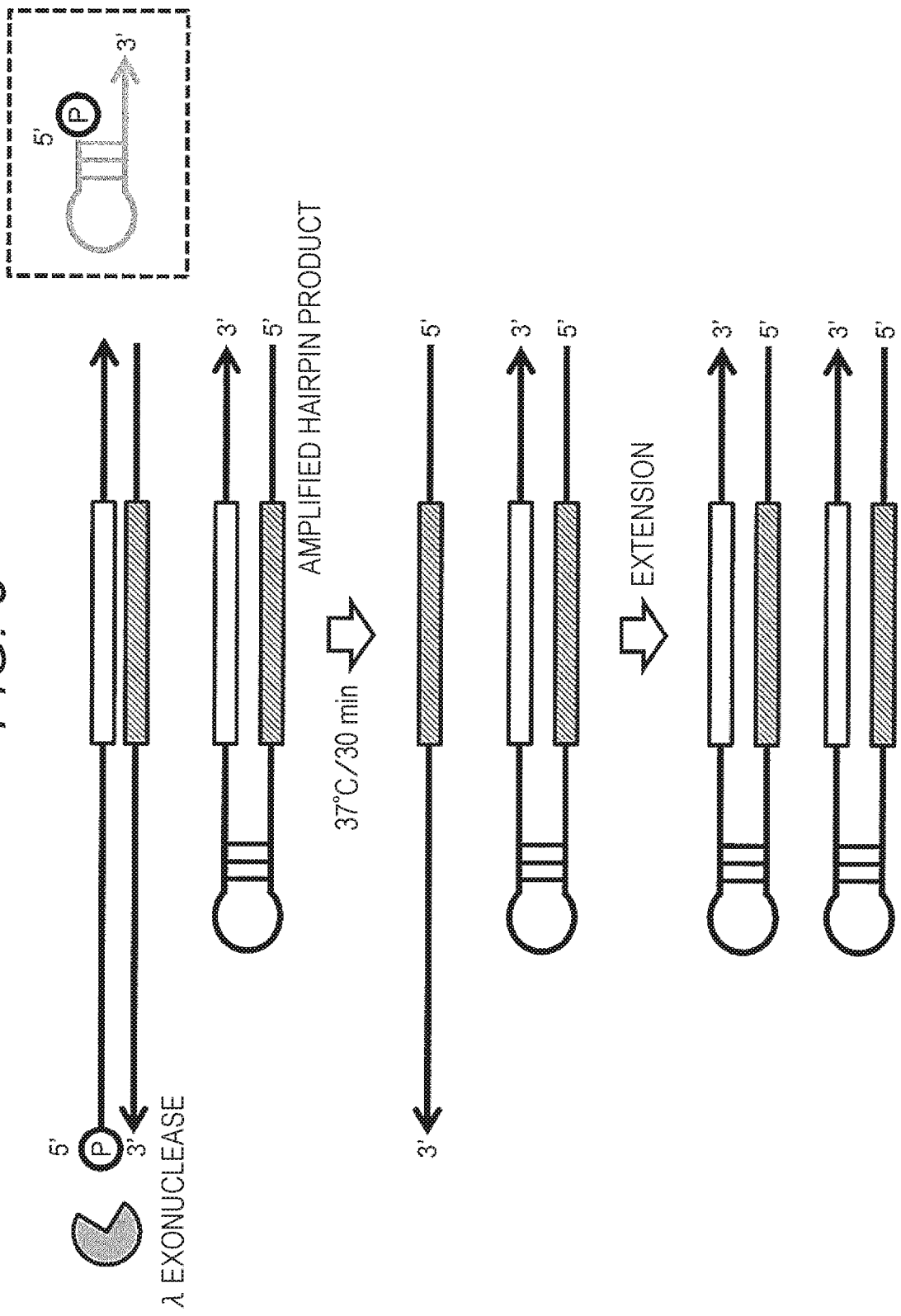
FIG. 5 is an example illustrating the nucleic acid molecule constructing step in the method of the present invention.

In this Example, an example of a method for constructing a molecule in which the total molecule includes the target sequence information twice will be described by using λ exonuclease. FIG. 5 illustrates procedures thereof.

This embodiment has a feature in that the 5' terminal of the hairpin primer is phosphorylated before use and the 5' terminal decomposes the phosphorylated DNA strand after constructing a target nucleic acid molecule. For decomposing, although there is no particular limitation, for example, λ exonuclease is used.

A step similar to FIG. 3 is performed before the step illustrated in FIG. 5. The step similar to FIG. 3 is different from the step of FIG. 3 in that the 5' terminal of the hairpin primer 300 is phosphorylated and then the amplification step illustrated in FIG. 3 is performed without the primer 303 in a pair being phosphorylated. After the reaction, if necessary, the salt and the primer in the amplification reaction solution are removed. The removing method is not limited, but for example, it is possible to use NUCLEOSPIN (registered trademark) Gel and PCR Clean-up (produced by Takara Bio Inc.) that is a commercially available kit immobilizing an amplified product to a silica membrane and performing purification by centrifugation.

The λ exonuclease is an enzyme that has a feature which digests from the phosphorylated 5' terminal side of a double-stranded DNA and discharges mononucleotide. The double-stranded DNA in which the 5' terminal is phosphorylated becomes a favorable matrix. By utilizing this property, λ exonuclease (produced by NEB) is added to an amplified product, a reaction solution is prepared with a buffer composition of 67 mM glycine-KOH (pH 9.4), 2.5 mM $MgCl_2$, and 50 µg/ml BSA, and then incubation is performed at 37° C. for 30 min. Through this reaction, a strand, which has a phosphate group of the double-stranded DNA which does not form a hairpin structure so that the target sequence information cannot be read twice in the single molecule, among amplified products generated through the process of FIG. 3 is digested to be obtain a single strand. After performing the λ exonuclease reaction, the reaction of extending the DNA strand is performed again.

In this case, the solution subjected to the λ exonuclease reaction is adjusted, for example, to a solution having the following composition.
20 mM Tris-HCl (pH 8.5)
50 mM KCl
2 mM $MgCl_2$
200 µM each dNTP
5U $Pfu^{exo}$-DNA polymerase (polymerase not having 3'-5' exonuclease activity)

Then, the reaction is performed with the above-described composition under the following temperature conditions. A high-order structure is detangled by heating at 94° C. for 5 min. Thereafter, a hairpin structure is constructed by annealing a sequence site having a complementary strand of the 3' terminal at 95° C. for 30 sec and at 60° C. for 45 sec, and then the extension reaction is performed by heating at 72° C. for 90 sec or longer. This reaction is not limited to the reaction conditions described above. The temperature, the time, the cycle, and the like may be changed according to a target sequence and a sequence of a hairpin structure.

As a result, as illustrated in FIG. 5, it is possible to obtain only a single-stranded nucleic acid having a hairpin structure in which the target sequence is repeated as a DNA strand to be obtained. There is no description on a purification step of removing a salt or an enzyme between reaction processes of respective steps, but if necessary, the purification step may be performed.

Similarly, in the nucleic acid molecule produced in this Example, a target sequence can be detected twice at the time of sequencing, and thus base sequencing with high precision can be performed.

Example 4

Figure 6:
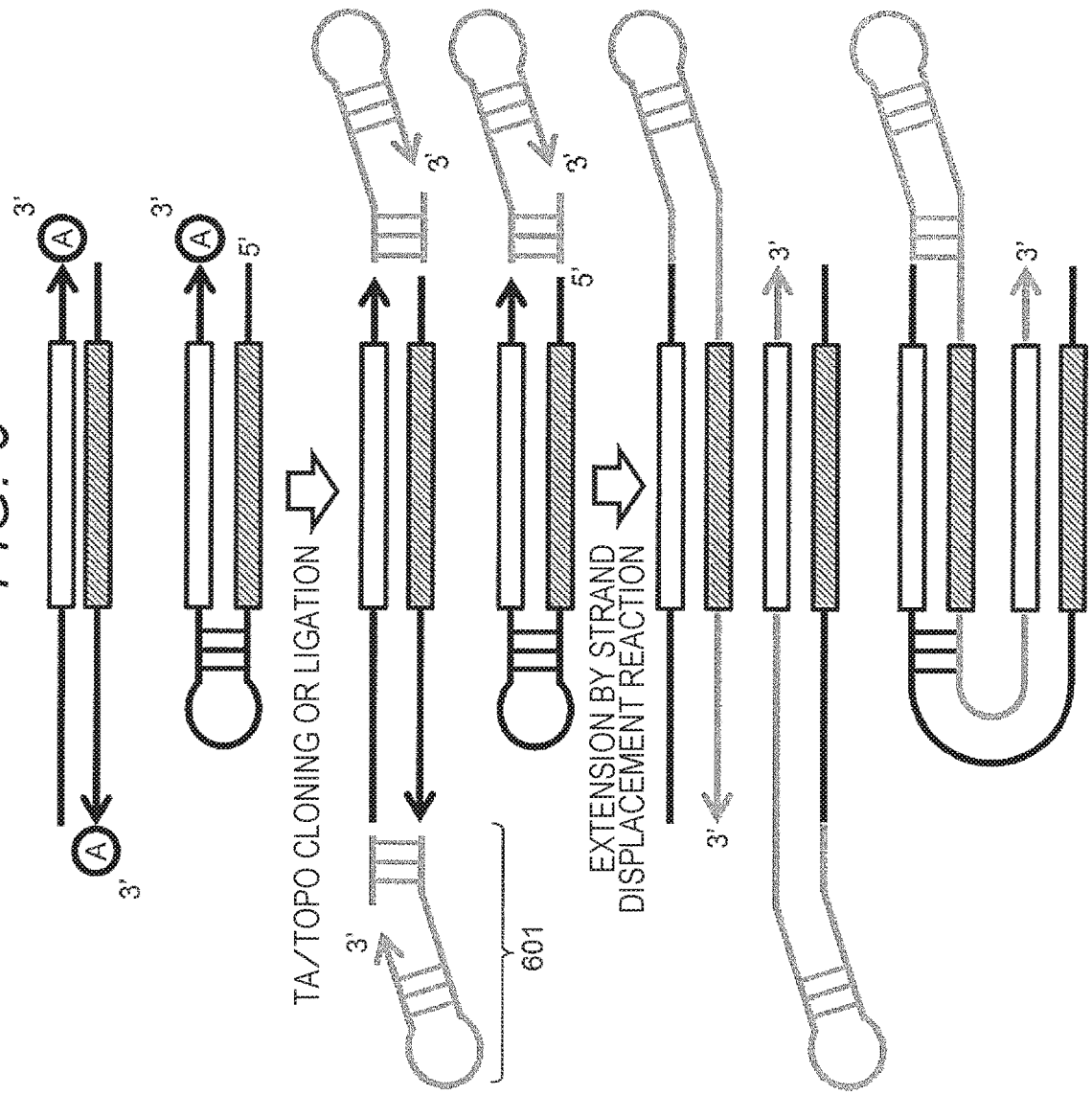
FIG. 6 is an example illustrating the nucleic acid molecule constructing step in the method of the present invention.

In this Example, a constructing method in which the target sequence can be detected four times as well as twice or more will be described. FIG. 6 illustrates procedures thereof.

A step similar to FIG. 3 is performed before the step illustrated in FIG. 6. The step similar to FIG. 3 is different from the step of FIG. 3 in that the step of performing the extension reaction "at 72° C. and for 90 sec" is performed for a sufficiently long time (for example, 5 min or longer), and thus it is possible to intentionally form a structure in which one adenine of the 3' terminal of the reaction product protrudes. For doing this, it is preferable to perform the extension reaction by using a DNA polymerase (for example, a Taq DNA polymerase) having terminal transferase activity.

TA cloning of connecting an adapter 601, which has a terminal structure in which one thymine base protrudes and a hairpin structure on the 3' terminal, to the reaction product formed herein is performed. This adapter 601 has, as illustrated in FIG. 6, a structure connected by only a single strand between a part (a double-stranded DNA) to be bound (ligated) to the reaction product in the previous step and a part forming a hairpin loop (for example, a sequence presented in Table 1). This is a structure in which the 3' terminal toward a part to be bound to the reaction product from the hairpin loop is disconnected.

As a connection example of the adapter, binding with the adapter 601 by the TA cloning is mentioned, but the connecting method is not limited thereto. For example, connection may be carried out, for example, by using other cloning techniques such as StrataClone PCR cloning system (Agilent Technologies) using DNA topoisomerase I and bacteriophage P1-derived Cre recombinase and TOPO (registered trademark) Cloning (Life Technologies), as a cloning system using a topoisomerase, for example.

As a step after connection, the extension reaction is performed by using a strand displacement type polymerase on the connected reaction product. Through this reaction, a base pair bond can be formed with respect to a complementary base sequence from the 3' terminal of the adapter 601 and incubation is performed at temperature at which enzymatic activity by which strand displacement reaction occurs may be maintained (for example, 60° C.). The time for incubation may be adjusted by the length of a base to be subjected to the extension reaction. Herein, the conditions in which a base pair bond is formed at each site generally include, for example, setting a temperature to be equal to or lower than a melting temperature, and are the same as the conditions to be used in a PCR method or LAMP method.

The extension by the strand displacement reaction may be carried out under the conditions in which a buffering agent providing pH suitable for an enzyme, a salt component used for maintaining the catalytic property of an enzyme and annealing, a protective agent for an enzyme, and if necessary, an adjusting agent for a melting temperature, and the like are caused to coexist. As an example of a pH buffering agent, those having an action of buffering a pH of a neutral to weakly alkaline value such as Tris-HCl may be used. The pH is adjusted according to the characteristics of an enzyme (DNA polymerase) to be used. As a salt component, KCl, NaCl, $(NH_4)_2SO_4$, or the like may be appropriately added in order to maintain the enzymatic activity and adjust the melting temperature of the nucleic acid. For protection of the enzyme, saccharides and bovine serum albumin may be used.

For adjusting the melting temperature, dimethylsulfoxide (DMSO) or formamide is generally used. By using these components as a melting temperature adjusting agent, the annealing from the 3' terminal can be adjusted under the restricted temperature condition. Further, betaine (N,N,N-trimethylglycine) is a natural permeable protective agent, and it is possible to use a property by which a melting temperature of the region in which a large number of G+C base sequence thereof is included is lowered to the same melting temperature of the region in which a large number of A+T base sequence is included. In addition, as a melting temperature adjusting agent, proline, trimethylamine N-oxide, or the like is known. The strand displacement efficiency can be improved by causing destabilization of the double-stranded DNA. The amount of betaine added in the reaction solution is 0.2 to 3.0 M and preferably about 0.5 to 1.5 M, and thus the promotive effect of the nucleic acid amplification reaction of the present invention can be expected. Since these melting temperature adjusting agents act to lower a melting temperature, the conditions under which a suitable reaction is performed are empirically set and carried out in consideration of other reaction conditions such as a salt concentration and a reaction temperature.

The extension reaction may proceed as long as the reaction is carried out by the characteristics of the strand displacement reaction. For example, there is mentioned a case where the 3' terminal structure leading the extension reaction is self-annealed or a case where the reaction proceeds by jumping to the adjacent base sequence of the 3' terminal structure itself.

In a case where the reaction proceeds in this way on the steric structure of the base sequence, ddNTP (dideoxyribonucleoside triphosphate) may be contained in a certain concentration in addition to dNTP (deoxyribonucleoside triphosphate) that is a matrix of the DNA polymerase. The length of the template to be amplified can be restricted according to the concentration of ddNTP to be contained. For example, if the extension reaction is continued through the loop structure, when a high concentration of ddNTP is contained, ddNTP is incorporated at the time of the strand displacement reaction and thus the extension reaction can be stopped. When the concentration of ddNTP is low, dNTP is preferentially incorporated into a polymerase, but when the strand displacement reaction proceeds to some extent to increase the concentration ratio of ddNTP, ddNTP is preferentially incorporated, and then the strand displacement reaction is stopped. The concentration of ddNTP may be adjusted according to a necessary extension product length. Depending on the concentration adjustment of ddNTP, the target sequence information can be repeated four times or more, but since an excessively repeated structure forms eventually a high-order structure so that the excessively repeated structure influences passing through the nanopore, the number of times of repeating may be differently set depending on the sequencing configuration.

The extension by performing the strand displacement reaction without limitation can also be controlled by using ddNTP as described above, but the control method is not limited thereto. As another example, when a part of a hairpin loop structure of the adapter 601 is configured to an abasic site, the reaction of the strand displacement type polymerase is stopped at the abasic site. Therefore, the length of the nucleic acid molecule generated by the abasic site can be controlled.

In addition, a molecule inhibiting the extension reaction by a polymerase can be contained in a hairpin loop structure part of the adapter 601. By preparing an inhibitor molecule, the extension reaction by a polymerase can be inhibited in the course of the extension reaction to prevent the extension without limitation. The structure of the inhibitor molecule is not particularly limited as long as the extension reaction by a polymerase can be inhibited, but for example, it is preferable to contain a nucleic acid derivative or a non-nucleic acid derivative.

In addition to the above-described abasic site, examples of the nucleic acid derivative include a nucleic acid having a structure that three-dimensionally inhibits the progress of polymerase, such as a tight high-order structure or a pseudo-knot structure which is not dissociated even by a strand displacement type enzyme, an L type nucleic acid, 3-deoxy-2-hydroxy-dN, a modified base nucleic acid, a damaged base nucleic acid, a nucleic acid containing a modified phosphate linkage, RNA, 2'-OMe-N, BNA (LNA), and derivatives of the foregoing.

As a result of the reaction described in this Example, as illustrated in FIG. 6, it is possible to obtain a single-stranded nucleic acid having a hairpin structure in which the target sequence is repeated four times. There is no description on a purification step of removing a salt or an enzyme between reaction processes of respective steps, but if necessary, the purification step may be performed.

In the nucleic acid molecule produced in this Example, a target sequence can be detected four times at the time of sequencing, and thus base sequencing with high precision can be performed.

Example 5

Figure 7:
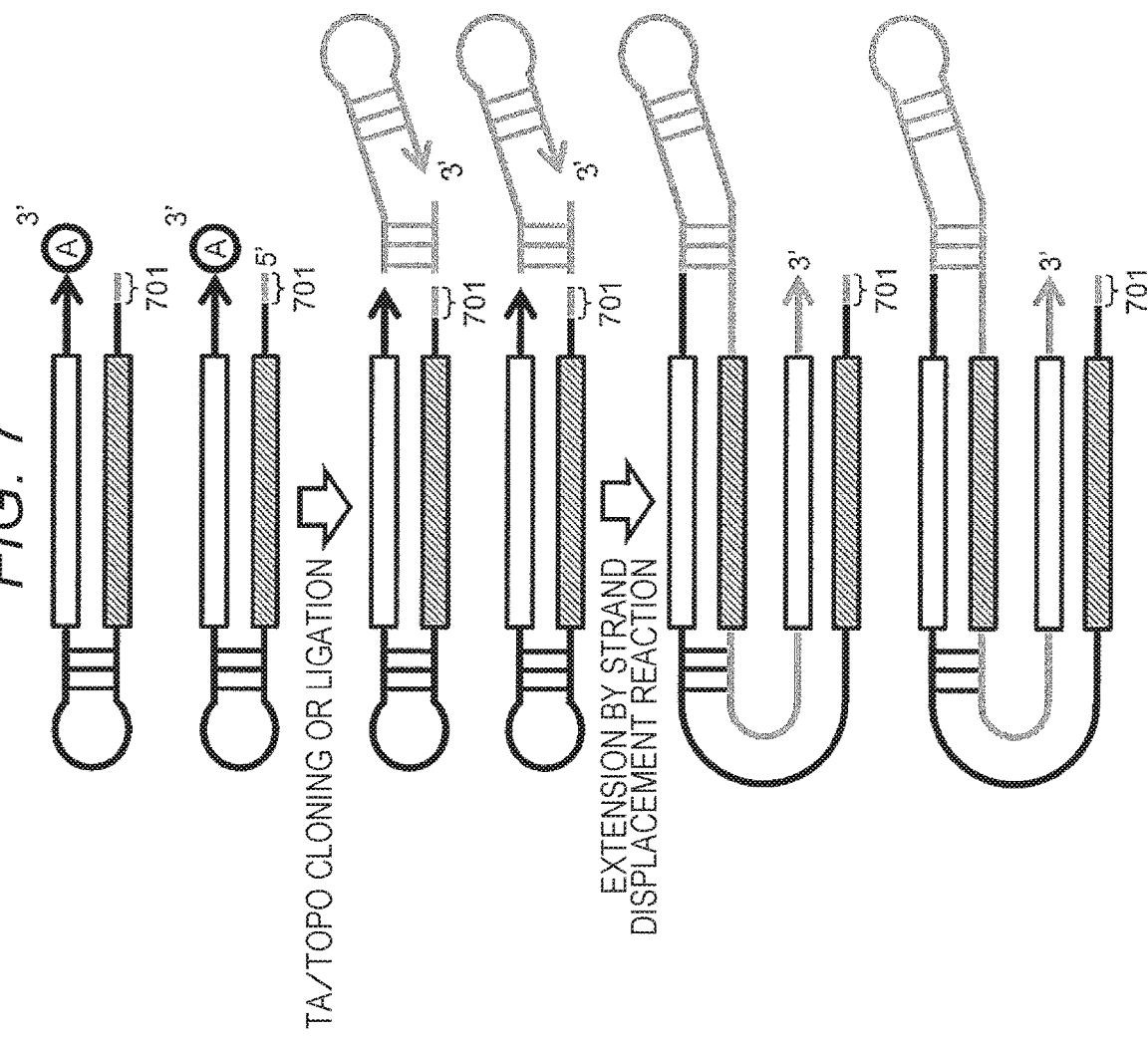
FIG. 7 is an example illustrating the nucleic acid molecule constructing step in the method of the present invention.

In the nucleic acid molecule constructed in Example 4, as illustrated in FIG. 6, a nucleic acid molecule in which the target sequence is repeated twice or four times may be mixed. In this Example, a method for constructing a nucleic acid molecule in which the total molecule includes a target sequence which is repeated four times will be described. FIG. 7 illustrates procedures thereof.

The step of FIG. 7 uses the reaction product generated by the reaction step illustrated in FIG. 5. This generated reaction product is a nucleic acid molecule in which the total molecule includes a target sequence which is repeated twice, and by using this, a nucleic acid molecule in which a target sequence is repeated four times is constructed.

Similarly to the example described in Example 4, in the reaction of FIG. 5, by sufficiently performing the extension reaction, it is possible to intentionally form a structure in which one adenine of the 3' terminal of the reaction product protrudes. Therefore, TA cloning, TOPO (registered trademark) cloning (Life Technologies), or the like in which the adapter 601 having the same structure as that used in Example 4 is provided to the reaction product generated in FIG. 5 is performed. However, the method for connection to the adapter is not particularly limited.

The reaction product of FIG. 5 and the adapter 601 are bound to each other, and then the extension reaction using a strand displacement type polymerase is performed. The reaction performed herein can form a base pair bond with respect to a complementary base sequence from the 3' terminal and performs incubation at temperature at which enzymatic activity by which strand displacement reaction occurs may be maintained. Herein, the conditions in which a base pair bond is formed at each site generally include, for example, setting a temperature to be equal to or lower than a melting temperature, and are the same as the conditions to be used in a PCR method or LAMP method. Also regarding the strand displacement reaction described herein, the reaction is performed in consideration of the same points as in the strand displacement reaction illustrated in Example 4.

As a result of the reaction described above, as illustrated in FIG. 7, the whole DNA strand to be obtained can be set to a single-stranded nucleic acid having a hairpin structure in which the target sequence is repeated four times. There is no description on a purification step of removing a salt or an enzyme between reaction processes of respective steps, but if necessary, the purification step may be performed.

In the nucleic acid molecule produced in this Example, a target sequence can be detected four times at the time of sequencing, and thus base sequencing with high precision can be performed.

Example 6

In Examples 1 to 5 described above, the step in which the nucleic acid molecule is mainly constructed has been primarily described. In Example 6, a constructing method which is made in consideration that the nucleic acid molecules constructed in Examples 1 to 5 are efficiently introduced to the nanopore will be described. The terminal structures of the nucleic acid molecules constructed by the methods of Examples 1 to 5 have a shape of a double-stranded DNA, and in a case where the base sequence of the single-stranded DNA is determined, by dissociating a double strand into a single strand, the introduction efficiency to the nanopore having a diameter size set to the single-stranded DNA is also improved. In general, in a case where a double-stranded DNA is denatured to a single-stranded DNA, the exposure to a solvent and high temperature, the adjustment of pH, the use of a melting temperature adjusting agent, and the like are well known techniques. A method of complementing these effects will be described in this Example.

The terminals of the molecules generated by the method for constructing a nucleic acid molecule illustrated in Examples 1 to 5 have a structure of a double-stranded DNA having the sequence of the primer 303 in a pair with the hairpin primer 300, for example, in the reaction illustrated in FIG. 3, and thus without any change, it is not easy to introduce the molecules to the nanopore having a diameter size of the single-stranded DNA. In this regard, when the sequence of this primer 303 is set to a sequence 701 (FIG. 7) enriched in an AT (adenine and thymine) sequence that is likely to become a single-stranded DNA at the time of denaturalization, the single-stranded DNA is easily introduced to the nanopore structure at the time of base sequencing.

Alternatively, the reaction illustrated in FIG. 3 is performed by using a chimeric primer of DNA having RNA on the 5' terminal of the hairpin primer 300 and RNA, and the reaction illustrated in each Example is performed. Thereafter, by using RNase H of ribonuclease, the RNA at the chimeric structure terminal is decomposed with the DNA and the RNA to generate a nucleic acid molecule in which a single-stranded DNA protrudes, and thus introduction to the nanopore from the site of the single-stranded DNA becomes easier.

Example 7

In this Example, a method will be described in which, by causing the hairpin primer 300 to have a random sequence 801, a nucleic acid molecule which is a derivation origin at the time of amplification is recognized by the random sequence 801, and the degree of determination precision of the sequence of the nucleic acid molecule that is a derivation origin is increased.

In the reactions illustrated in Examples 1 to 6, the hairpin primer 300 is caused to have the random sequence 801. For example, as illustrated in FIG. 8A, the random sequence 801 is designated as the site of the double strand formation sequence of the hairpin primer 300. In the site other than the sequence complementary to the target sequence, when the random sequences of 10 base pairs are formed in the double strand formation sequence (stem part), a hairpin primer having $4^{10}$ (1,048,576) types of random sequence in four types of base can be prepared. As a result, in the steps of FIG. 8A (1) to FIG. 8C (5), a nucleic acid molecule to be amplified with a nucleic acid molecule, which is copied by using a certain random sequence 801, as a template is amplified as a molecule having the same random sequence 801 and a complementary sequence 802 thereof as illustrated in FIG. 8C (5). By repeating the amplification cycle, an exponentially amplified nucleic acid molecule is obtained while the sequence that is a derivation origin of amplification and the random sequence are maintained. The nucleic acid molecules to be amplified from hairpin primers 803 to 805 each having a different random sequence form a nucleic acid molecule group having a different random sequence (FIG. 8C).

At the time of the sequence analysis, when the target sequence and the site corresponding to the double strand formation sequence of the hairpin primer 300 (the random sequence 801 and the complementary sequence 802 thereof) are recognized, the same number of analysis results of the sequence of the nucleic acid molecule that is a derivation origin at the time of amplification as only the number of the amplified nucleic acid molecules is obtained. Thus, it is possible to increase the precision of determination on whether there is a base sequence reading error or a mutation with respect to reference sequences in database or the like.

In FIG. 9, the sequence analysis results of a plurality of nucleic acid molecules (01 to 05) having the same random sequence 901 are collectively presented, and an example of the comparison result of target sequences is presented. When the analysis result of each nucleic acid molecule and the reference sequences are compared with each other, different results between molecules are detected. In this case, if the result is a reading error at the time of the sequence analysis, the existence of a base different from a reference sequence is presented at a random position of a part of the nucleic acid molecule (a base surrounded by the square in the drawing). For example, in a case where the analysis result is "G" in the amplified nucleic acid molecule 01 and the analysis result is "C" in other nucleic acid molecules 02 to 05, this case is determined to be a reading error ("C" also in the reference sequence). On the other hand, in a case where a mutation occurs in the base sequence of the nucleic acid molecule that is a derivation origin of amplification ("T"→"C" in a position 902), a base different from the reference sequence is shown in the position 902 of the nucleic acid molecules 01 to 05 having the same random sequence 901 (a base that is commonly different among nucleic acid molecules 01 to 05). That is, the nucleic acid molecule that becomes a derivation origin of amplification is recognized, a large number of the nucleic acid molecule amplified from this molecule is read while being discriminated from the nucleic acid molecule that has a different derivation origin of amplification, and thus analysis with higher precision can be performed.

This technique is particularly effective in a case where a mutation derived from an abnormal cell which is slightly included in a genomic DNA derived from a large amount of normal cell is detected.

Herein, the base length of the random sequence 801 is set to 10 bases, but is not limited thereto. In a case where the proportion of the detection target included is small, when the base length of the random sequence is lengthened, a larger number of types of hairpin primer can be used in the reaction, and amplification can be carried out without using a hairpin primer which has a detection target (for example, a nucleic acid derived from an abnormal cell) and the same random sequence as another target (a nucleic acid derived from a normal cell). In other words, the hairpin primer preferably has the types of random sequence more than the number of mutations of the target sequence.

Incidentally, in FIGS. 8A to 8C, the position of the random sequence 801 is a site of the double strand formation sequence, but the random sequence may be formed while including the loop part of the hairpin. In addition, although not particularly limited, the base length of the stem part of the hairpin primer can be set to a range of 8 to 20 bases, for example, 16 to 18 bases.

All the publications, patents, and patent applications quoted in the present description are incorporated herein by reference in its entirety.

REFERENCE SIGNS LIST 100 nanopore Raman DNA sequencer
101 light source
102 objective lens
103 microscope observation container
104 XY stage
105 Z-axis adjustment mechanism
106 filter
107 beam splitter
108 diffraction grating
109 detector
110 LED
111 two-dimensional detector
112 mirror
113 multiple irradiation mechanism
114 lens
115 drive controller
116 computer
117 near-infrared (NIR) mirror
201 observation container
202 nanopore
203 substrate
204 sample introduction section
205 sample outflow section
206 inflow path
207 inflow path
208 outflow path
209 outflow path
210 liquid
211 liquid
212 sample
213 electrode
214 electrode
215 electrically conductive thin film
216 liquid immersion medium
217 objective lens
300 hairpin primer
300a extension product of hairpin primer 300
301 complementary strand sequence part forming hairpin structure
302 complementary strand sequence part in hairpin primer
303 primer
303a extension product of primer 303
303b extension product of primer 303
303c extension product of primer 303
303d extension product of primer 303
601 hairpin adaptor
701 sequence enriched in AT (adenine and thymine) sequence
801 random sequence
802 complementary sequence of random sequence
803 hairpin primer having different random sequence
804 hairpin primer having different random sequence
805 hairpin primer having different random sequence
901 random sequence
902 base that is commonly different among nucleic acid molecules 01 to 05

The invention claimed is:

1. A method for constructing a single-stranded nucleic acid molecule, the method comprising: synthesizing a complementary strand of a template DNA including a target sequence by using at least one hairpin primer including a single-stranded region at the 3' terminal end and a primer in a pair, wherein the hairpin primer comprise a stem region that has a Tm value at least 5° C. higher than the Tm value of the single strand region to form a hairpin structure from the synthesized complementary strand; and performing a template extension reaction on the hairpin structure to obtain the single stranded nucleic acid molecule wherein the obtained nucleic acid molecule includes both the target sequence and the complementary strand thereof in the sequence.

2. The method according to claim 1, wherein the synthesized complementary strand sequence performs a template extension reaction in accordance with a reduction in the hairpin primer due to the advance of the reaction.

3. The method according to claim 1, further comprising of phosphorylating the 5' terminal end of the hairpin primer before use and decomposing the phosphorylated DNA strand after constructing a target nucleic acid molecule.

4. The method according to claim 3, wherein the decomposition is performed by using λ exonuclease.

5. The method according to claim 3, wherein, the extension reaction of self-annealing from the 3' terminal end of the complementary strand thereof through the hairpin structure is performed after the phosphorylated DNA strand is decomposed.

6. The method according to claim 1, further comprising an adapter having a hairpin loop structure to the obtained nucleic acid molecule and performing a strand displacement reaction to extend the obtained nucleic acid molecule.

7. The method according to claim 5, wherein an adapter having a hairpin loop structure is ligated to the obtained nucleic acid molecule and performing a strand displacement reaction to extend the obtained nucleic acid molecule.

8. The method according to claim 1, wherein the 5' terminal end formed from the primer in the pair is immobilized and the template extension reaction is performed after the complementary strand DNA is dissociated.

9. The method according to claim 6, wherein a loop structure part of the adapter includes an extension reaction inhibitor molecule.

10. The method according to claim 1, wherein the primer in the pair has a chimeric structure of DNA and RNA, and the method further includes a step in which the RNA is decomposed after the extension reaction.

11. The method according to claim 1 further comprising sequencing the obtained nucleic acid molecule using a nanopore sequencer.

12. The method according to claim 11, wherein the sequencing step comprises obtaining a signal from a known base sequence in the nucleic acid molecule and correcting a detector based on the signal from the known base sequence.

13. The method according to claim 11, wherein the sequencing step, analysis is performed on the basis of a signal obtained from a known base sequence included in the nucleic acid molecule.

14. The method according to claim 11, wherein the speed of a reaction product passing through the nanopore is controlled by using a reaction product having a double strand formed therein.

15. The method according to claim 1, wherein the hairpin primer has a random sequence.

16. The method according to claim 15, wherein the hairpin primer comprises random sequences equal to or more than the number of mutations in the target sequence.

* * * * *

SEQUENCE LISTING

<160> NUMBER OF SEQ ID NOS: 8

<210> SEQ ID NO 1
<211> LENGTH: 32
<212> TYPE: DNA
<213> ORGANISM: Artificial
<220> FEATURE:
<223> OTHER INFORMATION: primer

<400> SEQUENCE: 1
accttctacc ctcagaaggt gaccaagttc at                               32

<210> SEQ ID NO 2
<211> LENGTH: 34

```
<212> TYPE: DNA
<213> ORGANISM: Artificial
<220> FEATURE:
<223> OTHER INFORMATION: primer

<400> SEQUENCE: 2
accttctata ccctcagaag gtgaccaagt tcat                               34

<210> SEQ ID NO 3
<211> LENGTH: 32
<212> TYPE: DNA
<213> ORGANISM: Artificial
<220> FEATURE:
<223> OTHER INFORMATION: primer

<400> SEQUENCE: 3
caccttcacc ctcagaaggt gaccaagttc at                                 32

<210> SEQ ID NO 4
<211> LENGTH: 24
<212> TYPE: DNA
<213> ORGANISM: Artificial
<220> FEATURE:
<223> OTHER INFORMATION: reference sequence

<400> SEQUENCE: 4
agtcagtcag tcagtcagtc agtc                                          24

<210> SEQ ID NO 5
<211> LENGTH: 32
<212> TYPE: DNA
<213> ORGANISM: Artificial
<220> FEATURE:
<223> OTHER INFORMATION: amplified nucleic acid molecule

<400> SEQUENCE: 5
agtgagtcag tcagccagtc agtcagattc gg                                 32

<210> SEQ ID NO 6
<211> LENGTH: 32
<212> TYPE: DNA
<213> ORGANISM: Artificial
<220> FEATURE:
<223> OTHER INFORMATION: amplified nucleic acid molecule

<400> SEQUENCE: 6
agtcagtcag tcagccagtc agtcagattc gg                                 32

<210> SEQ ID NO 7
<211> LENGTH: 32
<212> TYPE: DNA
<213> ORGANISM: Artificial
<220> FEATURE:
<223> OTHER INFORMATION: amplified nucleic acid molecule

<400> SEQUENCE: 7
agtcagtctg tcagccagtc agtcagattc gg                                 32

<210> SEQ ID NO 8
<211> LENGTH: 32
<212> TYPE: DNA
<213> ORGANISM: Artificial
```

-continued

```
<220> FEATURE:
<223> OTHER INFORMATION: amplified nucleic acid molecule

<400> SEQUENCE: 8
agtcagtcag tcagccagtc aggcagattc gg                                    32
```